United States Patent
Weber

(10) Patent No.: US 8,795,494 B2
(45) Date of Patent: Aug. 5, 2014

(54) METHODS AND APPARATUS FOR CARRIER-FREE DEFLECTION ELECTROPHORESIS

(75) Inventor: Gerhard Weber, Kirchheim (DE)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 12/911,280

(22) Filed: Oct. 25, 2010

(65) Prior Publication Data

US 2011/0174624 A1 Jul. 21, 2011

Related U.S. Application Data

(63) Continuation of application No. 11/846,718, filed on Aug. 29, 2007, now abandoned.

(60) Provisional application No. 60/823,833, filed on Aug. 29, 2006, provisional application No. 60/883,260, filed on Jan. 3, 2007.

(51) Int. Cl.
*G01N 27/447* (2006.01)
*G01N 27/453* (2006.01)
*B01D 57/02* (2006.01)

(52) U.S. Cl.
USPC ............ 204/450; 204/600; 204/644; 204/645

(58) Field of Classification Search
USPC ............ 204/403.01–403.15; 205/777.5, 778, 205/792; 435/4–40.52, 287.1–288.7
See application file for complete search history.

(56) References Cited

U.S. PATENT DOCUMENTS

| | | | |
|---|---|---|---|
| 2,878,178 A | 3/1959 | Bier | |
| 3,140,714 A * | 7/1964 | Murphy, Jr. et al. | ......... 604/6.01 |
| 3,519,549 A | 7/1970 | Grassmann et al. | |
| 3,692,654 A | 9/1972 | Svendsen | |
| 3,847,773 A | 11/1974 | Snyder | |
| 3,869,365 A | 3/1975 | Sunden | |
| 4,061,560 A | 12/1977 | Hannig et al. | |
| 4,309,268 A | 1/1982 | Richman | |
| 5,173,164 A | 12/1992 | Egen et al. | |

(Continued)

FOREIGN PATENT DOCUMENTS

| | | |
|---|---|---|
| JP | 4233450 A | 8/1992 |
| JP | 5-080032 A | 3/1993 |

(Continued)

OTHER PUBLICATIONS

Giannovario et al., "A Mathematical Model of Free-Flow Electrophoresis", Journal of Chromatography, vol. 153, 1978, pp. 329-352, Elsevier Scientific Publishing Company, Amsterdam.

(Continued)

*Primary Examiner* — Susan D Leong
(74) *Attorney, Agent, or Firm* — The Webb Law Firm

(57) ABSTRACT

The invention relates to a method and apparatus for carrier-free deflection electrophoresis, in which a separating media and a sample to be examined flow through a separating chamber between a pair of electrodes in a series of reversing bulk fluid flow along the direction of the electrodes, thereby separating the sample into zones which are to be collected into fractions for analysis or further processing. Among other things, the apparatus and method enable high-resolution separation of particles that can be performed in miniaturized chambers in electrophoresis modes including isoelectric focusing, zone electrophoresis, and isotachophoresis.

26 Claims, 13 Drawing Sheets

(56) References Cited

U.S. PATENT DOCUMENTS

| | | |
|---|---|---|
| 5,180,480 A | 1/1993 | Manz |
| 5,275,706 A | 1/1994 | Weber |
| 5,277,774 A * | 1/1994 | Shmidt et al. ............... 204/545 |
| 5,562,812 A | 10/1996 | Carlson et al. |
| 6,328,868 B1 | 12/2001 | Weber |
| 7,052,589 B1 * | 5/2006 | Vigh ............................ 204/451 |
| 7,316,771 B2 | 1/2008 | Weber |
| 7,399,394 B2 | 7/2008 | Weber |
| 7,491,304 B2 | 2/2009 | Weber |
| 7,597,791 B2 | 10/2009 | Huang et al. |
| 2004/0050697 A1 * | 3/2004 | Eckerskorn et al. .......... 204/450 |
| 2004/0178865 A1 * | 9/2004 | Snyder et al. ................ 333/156 |
| 2005/0130157 A1 * | 6/2005 | Serwer et al. ..................... 435/6 |
| 2007/0227891 A1 * | 10/2007 | Tsai et al. ..................... 204/457 |

FOREIGN PATENT DOCUMENTS

| | | |
|---|---|---|
| JP | 2002506204 A | 2/2002 |
| WO | 2006/119001 A1 | 11/2006 |
| WO | 2006118996 A2 | 11/2006 |

OTHER PUBLICATIONS

Boese, "Contributions to a Mathematical Theory of Free-Flow Electrophoresis", Journal of Chromatography, vol. 438, 1988, pp. 145-170, Elsevier Scientific Publishersm B.V., Amsterdam.

Roman et al., "Free-Flow Electrophoresis", Analytical Chemistry, vol. 66 No. 2, Jan. 15, 1994, pp. 86-94.

* cited by examiner

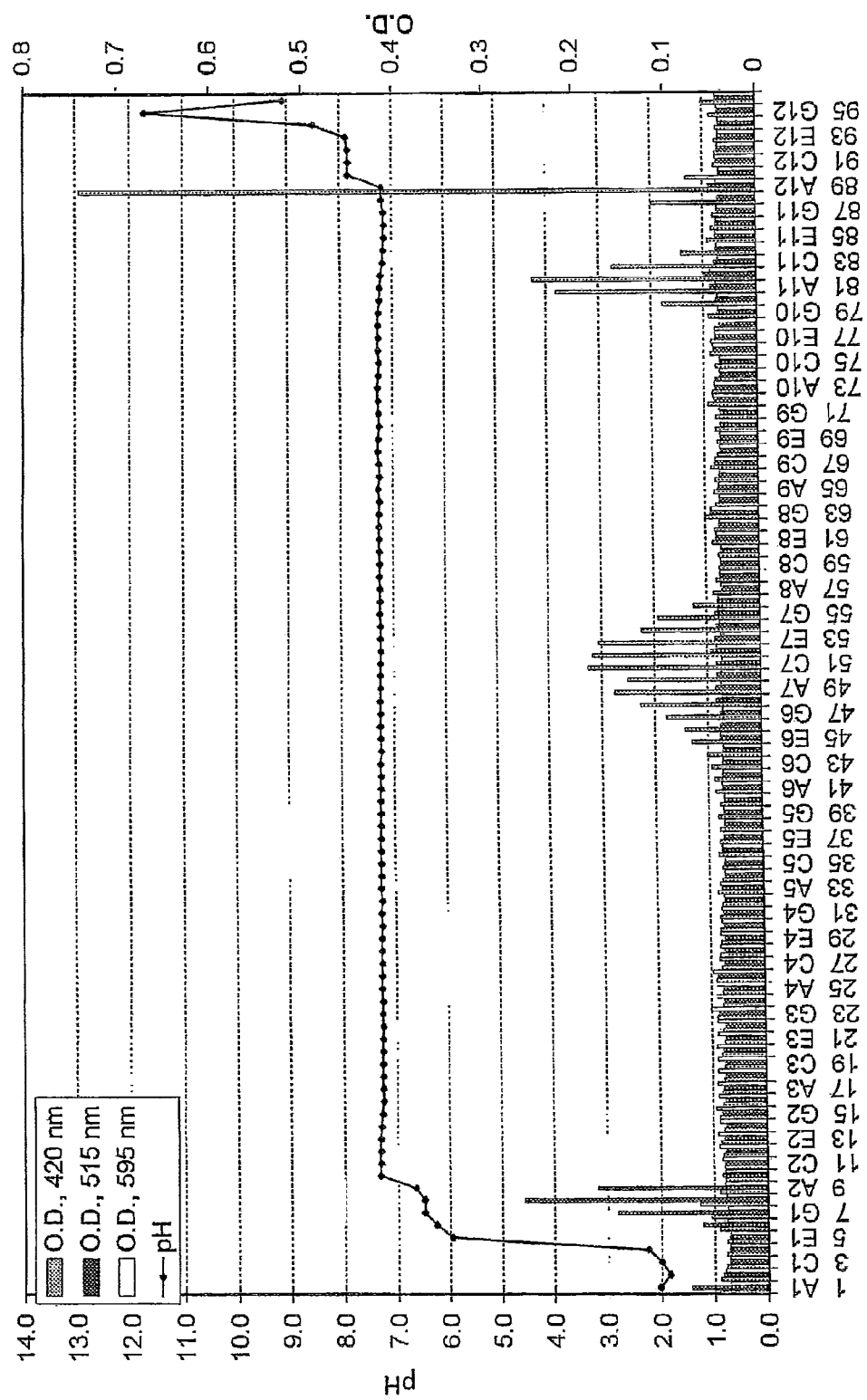
FIG. 5 --PRIOR ART--

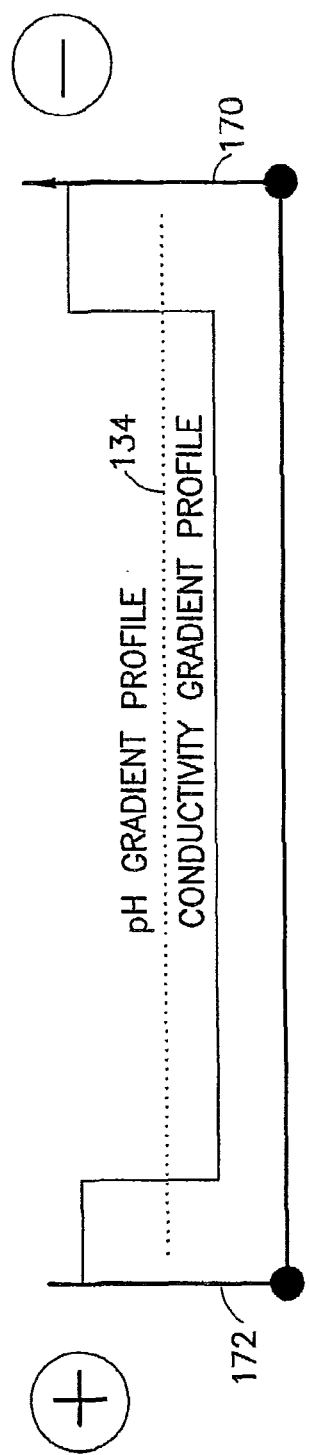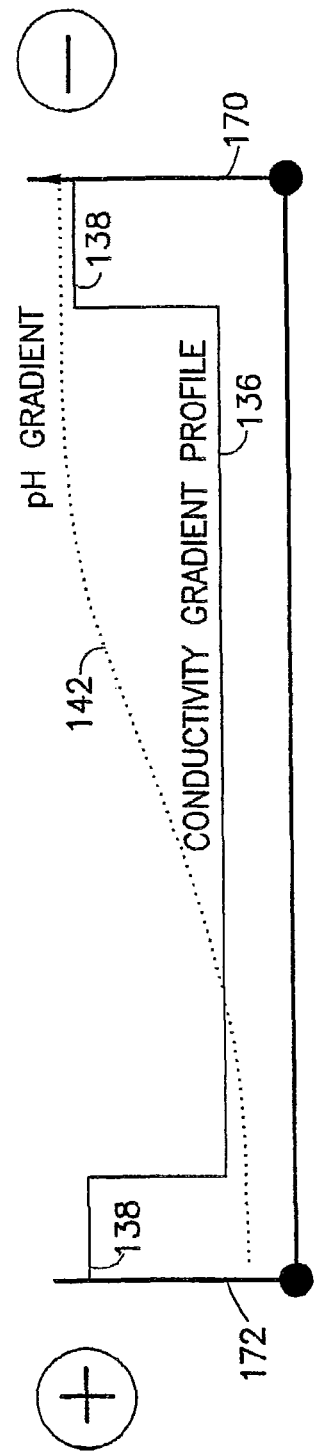

METHODS AND APPARATUS FOR CARRIER-FREE DEFLECTION ELECTROPHORESIS

This patent application claims priority to U.S. Provisional Patent Application Ser. No. 60/823,833 filed on Aug. 29, 2006 and U.S. Provisional Patent Application Ser. No. 60/883,260 filed on Jan. 3, 2007.

FIELD OF THE INVENTION

The invention relates to carrier-free deflection electrophoresis, including an apparatus and method for carrying out the same.

BACKGROUND OF THE INVENTION

The basics of carrier-free deflection electrophoresis, especially with respect to continuously operated processes, have been described in the literature over 30 years ago. The process is sometimes described under the term FFE (free flow electrophoresis) or more commonly CFE (continuous flow electrophoresis). (K. Hannig: Carrier-free continuous electrophoresis and its application. Anal. Chem. 181, 233 (1961); M. C. Roman and P. R. Brown: Anal. Chem. Free Flow Electrophoresis. 66(N2), 86-94, (1994); R. Braun, H. Wagner and G. Weber: Preparative Free Flow Electrophoresis—a powerful procedure for separating natural substances, GIT Fachzeitschrift für das Laboratorium 39 (1995), 317-322).

Generally, FFE separation procedures are used to separate ions of any molecular weight up to bioparticles. It is here irrelevant whether the sample to be separated is charged itself, or whether the charge came about via the addition or sorption of ions.

Carrier-free deflection electrophoresis has traditionally been used in continuous processes commonly referred to as continuous free-flow electrophoresis (CFFE). This method used in absence of a support matrix such as a gel enables the separation, fractionation, and possible isolation of both soluble and insoluble components. In comparison to other methods enabling isolation of separated sample components, continuous free-flow electrophoresis generally offers three main advantages: (i) the sample is maintained in a liquid medium/in solution which can be directly used for further processing, (ii) the separation may be performed continuously and enables one to obtain as much as hundreds of milligrams or even gram amounts of pure substances per hour and (iii) the separation is gentle and preserves biological activity of the separated components.

The technology of FFE is particularly useful in the separation and fractionation of complex proteins, and is thus applicable to the emerging field of proteomics, which is growing increasingly important in academic and pharmaceutical research as well as the general biotechnology and clinical diagnostic markets. For example, as proteomic research has grown, there has been an increased demand in the improvement of protein separation performance or resolution, especially in terms of resolution process reliability. There has also been demand for a universal front-end separation system and method that occurs prior to a later analysis or further separation/fractionation step.

Improvements to the field of FFE have come about. For example, the process of continuous deflection electrophoresis (or continuous free-flow electrophoresis) has been improved by way of stabilization media and counter-flow media. This is reflected, for example, in U.S. Pat. No. 5,275,706, the disclosure of which is hereby incorporated by reference in its entirety. According to this patent, a counter-flow medium is introduced into the separation space counter to the continuous flow direction of the bulk separation medium and sample that travels between the electrodes. Both media (separation media and counterflow media) are discharged or eluted through fractionation outlets typically into a microtiter plate, resulting in a fractionation process having a low void volume. Additionally, a laminar flow of the media in the region of the fractionation outlets is maintained (i.e., with very low or no turbulence).

Additionally, free-flow deflection electrophoresis has been implemented in a non-continuous or interval process. For example, a process of non-continuous deflection electrophoresis is shown in U.S. Pat. No. 6,328,868, the disclosure of which is hereby incorporated by reference. In this patent, the sample and separation medium are both introduced into an electrophoresis chamber, and then separated using an electrophoresis mode such as zone electrophoresis, isotachophoresis, or isoelectric focusing, and are finally expelled from the chamber through fractionation outlets. Embodiments of the '868 patent describe the separation media and sample movement to be unidirectional, traveling from the inlet end towards the outlet end of the chamber, with an effective voltage applied causing electrophoretic migration to occur while the sample and media are not being fluidically driven from the inlet end towards the outlet end. Examples of embodiments of the '868 patent are shown in FIG. 1.

Both above examples of FFE (i.e., continuous and non-continuous or interval mode) can be used in certain situations, with each experimental goal having factors and requirements or specifics that lend one to prefer one process to the other. Such factors include the choice of sample intended to be separated including required or desired separation time, sample size, separation resolution desired, chamber size, etc. These and other factors influence the mode of separation as well as the apparatus, specific methods, techniques, and compositions to be used. One or more of these above factors may or may not influence which mode of operation (continuous or non-continuous) is chosen when both are available to the user given a certain situation and experimental or separation goal. It should be noted that while using free-flow electrophoresis, both in continuous and non-continuous (or interval) modes of operation, each may have many benefits when compared to other separation or fractionation methodologies and techniques. Nevertheless, improvements are always desired.

Numerous publications describe the physical or electrochemical effects that contribute to the so-called "band widening" of the analytes during separation in continuous free-flow deflection electrophoresis (J. A. Giannovario, R. Griffin, E. L. Gray: A mathematical model of free-flow electrophoresis. Journal of Chromatography, 153, 329-352 (1978); F. G. Boese: Contribution to a mathematical theory of free flow electrophoresis, J. Chromat. 483, 145-170 (1988); K. Hannig and H. G. Heidrich: Free-Flow Electrophoresis, 1990 by GIT Verlag Darmstadt ISBN 3-921956-88-9).

The most important of these effects inherent in continuous FFE are:
 1. band widening due to the laminar flow profile;
 2. band widening due to thermal convection;
 3. band widening due to electrical osmosis;
 4. band widening due to electrokinetic effects.

The negative influence of all electrokinetic effects described thus far can be minimized or eliminated by using separation media with suitable ionic constituents with sufficiently high ionic strength, and at the same time not excessively increasing the concentration of the sample.

There are numerous ways to minimize the negative influence of electrical osmosis, e.g., through the selection of a suitable wall material (plastics instead of glass or quartz), or most preferably by adding surface-active chemicals to the separation media that preclude electrical osmosis. This method is referred to as "dynamic coating" in the literature.

The negative influence of thermal convection can be reduced very easily by arranging and operating the electrophoresis chamber horizontally instead of vertically. Additionally, thermal effects can be minimized by appropriate cooling and maintaining the electrophoresis chamber at a constant temperature throughout the separation process.

The negative influence of the laminar flow profile is not observed for continuous isoelectric focusing (IEF) as long as a sufficiently long separation time is selected that also enables the focusing of the analytes, which are transported at the highest linear velocity in the center of the electrophoresis chamber gap.

By contrast, the negative influence is very significant in the case of the electromigration processes. Analytes that migrate near or in the boundary surface to the walls of the electrophoresis chamber pass through the electrophoresis chamber in a considerably longer time than analytes at the center of the electrophoresis chamber gap, and are therefore deflected to a clearly greater extent due to their longer residence time. This effect results in a band widening detectable as a tailing in the direction of electromigration.

Given a continuously executed electromigration process under the boundary conditions of carrier-free electrophoresis, the negative influence of the laminar flow profile cannot be averted for low-molecular analytes. The absolute value of band widening increases as does the migration distance of the analytes. Reducing the diffusion rates for analytes that have their migration impacted by using separation media with increased viscosity also does not help, since this magnifies the unfavorable nature of the laminar flow profile.

In the case of separation of bioparticles, a quantitatively reduced sample feeding to the center of the electrophoresis chamber gap can result in an improved resolution, since the particles cannot get into the area of the electrophoresis chamber walls during a retention time of <10 minutes due to the extremely low diffusion. However, the influence of laminar flow profile can only be minimized in this way by distinctly reducing the sample feeding rate (e.g., to a sample flow rate that is only 0.1% to 0.5% of the flow rate of the separation medium).

Compared to the continuous FFE operating modes known in the art, the interval FFE mode as described in U.S. Pat. No. 6,328,868 is capable of avoiding the negative influence of a laminar flow profile observed in electromigration processes.

However, there remains a need in the art for further improvements of the free-flow electrophoresis methods.

SUMMARY OF THE INVENTION

Accordingly, the object of the invention is to provide a method for carrier-free deflection electrophoresis, which eliminates the influence of a laminar flow profile typical of continuous free-flow electrophoretic separations and additionally increases separation quality and/or reducing the turn around time or reduction in fractionation time needed to obtain high resolution quality for electrophoretic separations. The method and device of the present invention can be used for both preparative and analytical separations.

Accordingly, in a first aspect, the present invention relates to a method for separating particles, wherein the method comprises disposing a separation medium and sample in an electrophoresis chamber having a top plate, a bottom plate and a plurality of electrodes generally parallel to one another with a separation space disposed therebetween, and a fluidic displacement system for conveying separation medium and sample particles between the electrodes, applying a voltage between the electrodes effective to manipulate particles electrophoretically, and wherein at least a portion of the separation medium and sample is displaced towards a first direction generally parallel to the direction of the electrodes, and subsequently in a second direction generally opposite the first direction.

In certain embodiments, the method for separating particles comprises disposing a separation medium and sample in an electrophoresis chamber having a top plate, a bottom plate, a first chamber end, a second chamber end, and a plurality of electrodes generally parallel to one another with a separation space disposed therebetween, the electrodes longitudinally extending toward each of the ends, and a fluidic displacement system for conveying a separation medium between the first and second chamber ends, applying a voltage between the electrodes effective to manipulate particles electrophoretically, displacing at least a portion of the separation medium and sample towards the first chamber end, displacing at least a portion of the separation medium and sample towards the second chamber end (i.e. reversal of the bulk flow), and optionally displacing at least a portion of the separation medium and sample towards the first chamber end, for example so as to dispel or elute at least a portion of the sample and/or separation medium through one or more outlets that are located at the chamber end opposite to the inlets. "Generally parallel" in the context of the present invention means that the bulk flow direction of at least the non-charged particles in the separation medium (e.g. water) is essentially parallel to the elongated electrodes. However, those of skill in the art will appreciate that charged species (i.e., sample or ions in the separation medium) within the electrophoresis chamber may at the same time also be deflected by the electrical field between the electrodes, thereby moving towards the cathode or anode and at the same time parallel to the electrodes towards the inlet or outlet end of the electrophoresis chamber. The movement of particles during a separation within a FFE apparatus is described in more detail further down below.

The present invention offers a distinct improvement in the quality of the electrophoretic separation, and in long-term stability and improved speed to achieve high resolution for the electrophoretic separation when compared to other separation techniques. In addition, the method of the present invention also offers increased flexibility regarding the design of the FFE devices used for the electrophoretic separations. Embodiments disclosed herein can be applied to most separation protocols that typically have been performed using continuous or static interval free flow electrophoresis applications generally known in the art and described hereinabove, including zone electrophoresis, isoelectric focusing and isotachophoresis.

Typically, chemical and physical discontinuities exist in electrophoretic chambers across the separation area and are well known sources of turbulences for liquids in the areas adjacent the migrating boundaries of the media, whereas non migrating boundaries (like boundaries between stabilizing media and separation media) will give rise to turbulences in case of overloading the separation process only (due to high field strength or to high current). It has now been found that the turbulences at migrating boundaries can be reduced substantially by shear forces, given by the vector of a linear movement of the separation media forward and backwards inside the separation cell with respect to the generally fixed electrophoresis chamber walls. The cycling back and forth, forward and backwards inside the separation cell with respect to generally fixed electrophoresis chamber walls is herein termed cyclic free-flow electrophoresis or, alternatively, cyclic interval free-flow electrophoresis.

For the purposes of the present invention, cyclic FFE includes at least one full cycle (i.e., moving separation medium and sample away from the sample and media inlets towards the opposite end of the FFE apparatus, then moving the sample and separation media in a second (typically opposite) direction, i.e., towards the inlet end of the FFE apparatus. In addition to the cycles during which electrophoretic separation of the sample particles is achieved, cyclic FFE may further comprise a stage wherein the direction is changed again towards the outlet end of the FFE apparatus in order to elute the sample and bulk separation media. Similarly, when the outlets are placed at or near the inlets of the apparatus, one full cycle is characterized by a single reversion of the flow direction, i.e. moving the separation medium and sample towards a first direction of the FFE apparatus, then moving the sample and separation media in a second (typically opposite) direction towards the inlet, and in this instance also outlet end of the FFE apparatus. The cycle described above may be repeated multiple times as further described hereinbelow, or may be carried out only once. Preferably, the method is supplemented by dispelling/eluting the sample and bulk separation media through one or more outlets.

In preferred embodiments, the number of cycles is greater than one, such as at least 2, 3, 4, 5, 6, 7, 8, 9 or 10 cycles, and is selected so as to achieve sufficient separation of the sample before the sample or at least fractions thereof is/are collected at the outlet end of the FFE apparatus. It will be understood by the skilled person that the number of cycles displacing the sample and the bulk separation medium back and forth depends on a number of factors, including sample size, quality of separation, electrophoretic mobility of the sample among others.

Electrophoretic mobility (EM), as used herein, means the rate of migration of anions and cations in an electrical field at a given field strength per time unit in an aqueous media. The electrophoretic mobility u can be calculated as follows:

$$u = s/H \times t$$

wherein s represents the distance of migration (m), H represents the electric field strength (V/m) and t represents the time (sec.).

An improved quality of separation is achieved using the novel method and apparatus according to embodiments of the present invention in combination with any of the known separation modes of free-flow electrophoresis, e.g., isotachophoresis (ITP), zone electrophoresis (ZE), and isoelectric focusing (IEF). Specifically, experiments have shown that the benefits of cyclic interval FFE are most valuable and surprising in the cases of cyclic FF-isotachophoresis and of cyclic FF-zone electrophoresis (for ZE, see FIGS. 5 and 6).

As mentioned above, U.S. Pat. No. 6,328,868 to Weber describes a method for carrying out matrix-free or free-solution electrophoresis between electrodes in a general interval manner. The interval mode described in the '868 invention generally introduces and elutes the sample and separation media in one direction. This direction, unlike traditional (gel and matrix-free) capillary electrophoresis wherein the sample moves in the same direction as the electric field through the capillary, is shared by the orientation of the elongated electrodes. An example of five stages (stages 0 through stage 4) demonstrating one exemplary embodiment of the '868 invention is shown in FIG. 1, as represented by FIGS. 1*a*-1*e* respectively. As shown in FIG. 1*a*, stage 0 comprises introducing a sample and separation media into the electrophoresis chamber with the flow on and the voltage off. As shown in FIG. 1*b*, stage 1 maintains the voltage off and the bulk flow of sample and separation media is stopped (flow off). As shown in FIG. 1*c*, stage 2 maintains the bulk flow off, but applies voltage between the electrodes causing electrophoretic separation. As shown in FIG. 1*d*, stage 3 turns the voltage off but forces the bulk flow of sample and separation media towards outlets opposite the inlets where the separation media was introduced. Finally, as shown in FIG. 1*e*, stage 4 turns the bulk fluid flow and voltage off. Stages 0-4 can then be repeated if so desired.

In the case of the '868 invention, displacement or acceleration of the sample caused by a pump or some other fluidic displacement element in the electrophoresis chamber between the electrodes only takes place when the voltage is off or at least when the voltage is ineffective for electrophoretic migration, i.e., when no part of the sample is being subjected to an effective electrophoretic field strength. Additionally, absolute displacement of the bulk sample and media in the '868 invention only occurs in the direction starting from the sample inlets and ending at the sample outlets. These two characteristics as well as other elements of the method and apparatus of the '868 invention were improved upon in the present invention.

Many advantages of the new FFE-process in cyclic interval mode according to embodiments of the present invention have been observed through a number of experiments.

First, because the sample and separation media is in motion during the electrophoretic separation stage, it is possible to apply higher field strengths. In view of the higher field strengths the new cyclic interval FFE-process will provide an enhanced performance, which can be used for a better discrimination of the analytes given the same duration of processing time that would be typical of the method described in U.S. Pat. No. 6,328,868 to Weber. Alternatively, the new method offers equal discrimination quality of the analytes but can be performed at a reduced duration of processing time when compared to continuous or standard interval free-flow electrophoresis methods. The latter advantage could enable higher throughput of distinct separations which may be applicable to an electrophoresis process used, e.g., in clinical proteomics.

Second, all conventional continuous FFE separation techniques and protocols may be easily adopted for use in the cyclic interval free-flow electrophoresis process.

Third, the method and apparatus according to embodiments of the present invention allows to extend the duration of electrophoretic separation of a sample in a chamber due to the periodic reversal of bulk sample flow. For instance, a continuous free-flow electrophoresis machine with a minimum bulk sample and separation media flow rate, controlled by a pump, has a minimum duration of travel that is a function of the viscosity, pump flow rate, shape of the chamber, and length from inlet to outlet. Unlike the continuous free-flow electrophoresis method, the cyclic interval method according to embodiments of the present invention, with the same minimum flow rate, viscosity, shape of chamber, and ability to reverse the fluid flow, can prolong the duration of travel between the sample inlets and outlets. This provides an opportunity for a prolonged time of separation which, for example, in the case of FF-isoelectric focusing is especially powerful and useful. Since the sample in the cyclic interval mode can be moved repeatedly in a forward and reverse direction, the effective travel length of the sample between the electrodes can be extended indefinitely. The prolonged time or extended distance of travel for separated particles will result in a better focusing of analytes, especially for those with a relatively low electrophoretic mobility.

Fourth, the new cyclic interval free-flow electrophoresis process can be utilized in separation chambers with many different options of geometric configuration and cross-section. This therefore enables flexibility for how one may implement FFE in miniaturized electrophoresis chambers, the shapes and sizes of which can be altered depending on the desired number of sample outlets for elution interposed between the pair or pairs of electrodes. Additionally, the length of the electrodes can be controlled or designed such that the amount of sample and separation media can be adjusted to account for the sample size or sample and analyte concentration that needs to be fractionated and/or detected.

The new cyclic interval FFE mode according to embodiments of the present invention can be used for specific applications hitherto inaccessible to free-flow electrophoretic separation technology. For example, the separation and isolation of protein isoforms with rather low speed of electrophoretic migration was difficult to achieve. With the method described herein, isolation of, e.g., such isoforms can be accomplished using the cyclic interval free-flow electrophoresis mode disclosed herein, which historically could not be realized using the continuous FFE-processes existing in the art. In addition, many other separation problems employing a variety of different samples have been successfully accomplished using the new cyclic interval FFE mode of the present invention.

The description below as well as the enclosed Figures exemplify several embodiments of the present invention.

BRIEF DESCRIPTION OF THE FIGURES

FIG. 5 demonstrates performance results of the prior art continuous FFE.

FIG. 9 describes various profiles of an embodiment of the present invention, wherein

FIG. 10 describes various profiles of another embodiment of the present invention, wherein

FIG. 11 describes various profiles of yet another embodiment of the present invention, wherein

DETAILED DESCRIPTION

Figure 1:
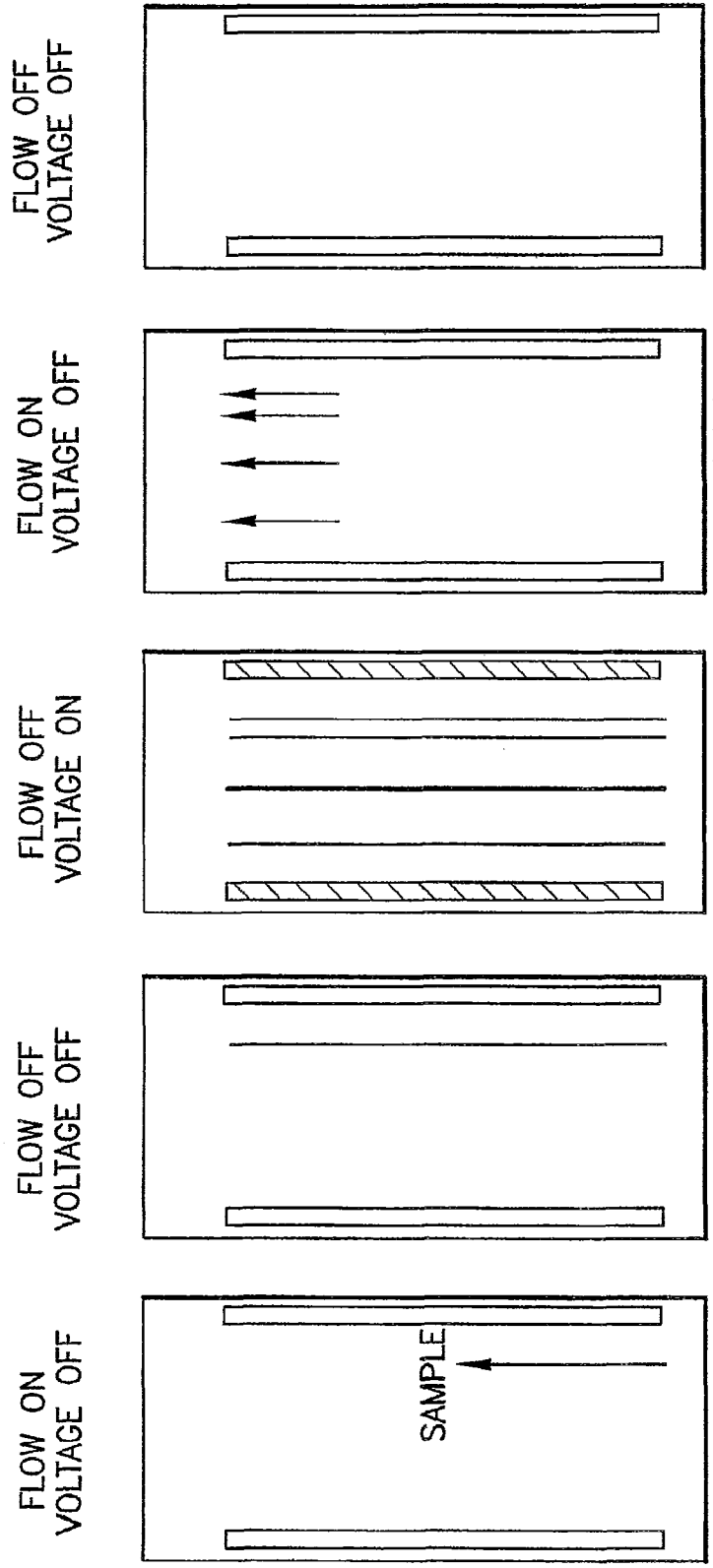
FIG. 1 describes steps for carrying out interval free-flow electrophoresis of the prior art.

The present invention and its advantages are further illustrated in the following, non-limiting examples. In the drawings, like reference characters generally refer to the same parts throughout the different views. Also, the drawings are not necessarily to scale, emphasis instead being placed upon illustrating the principles of the invention.

Figure 2:
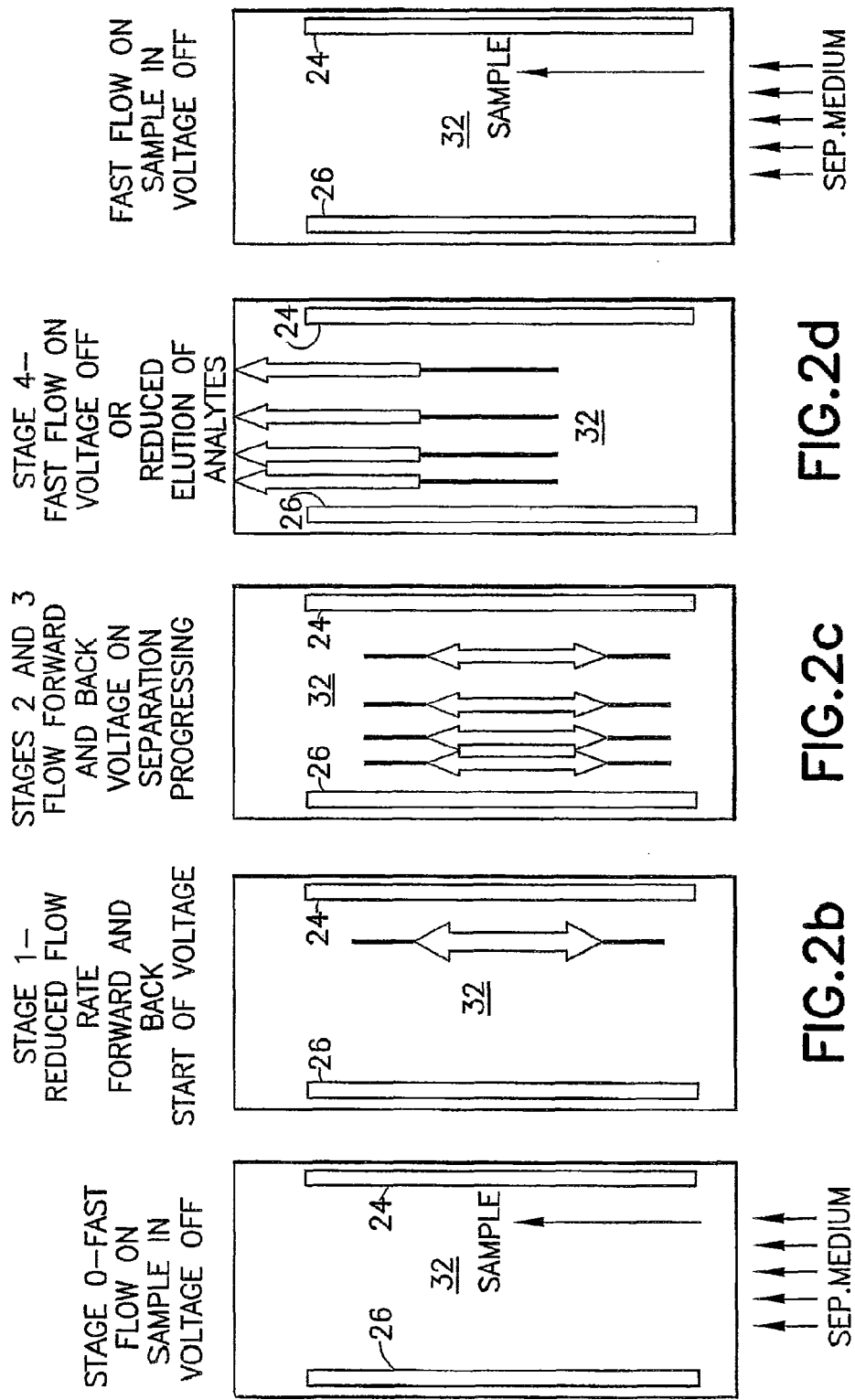
FIG. 2 describes steps for carrying out an embodiment of the present invention.
Figure 3:
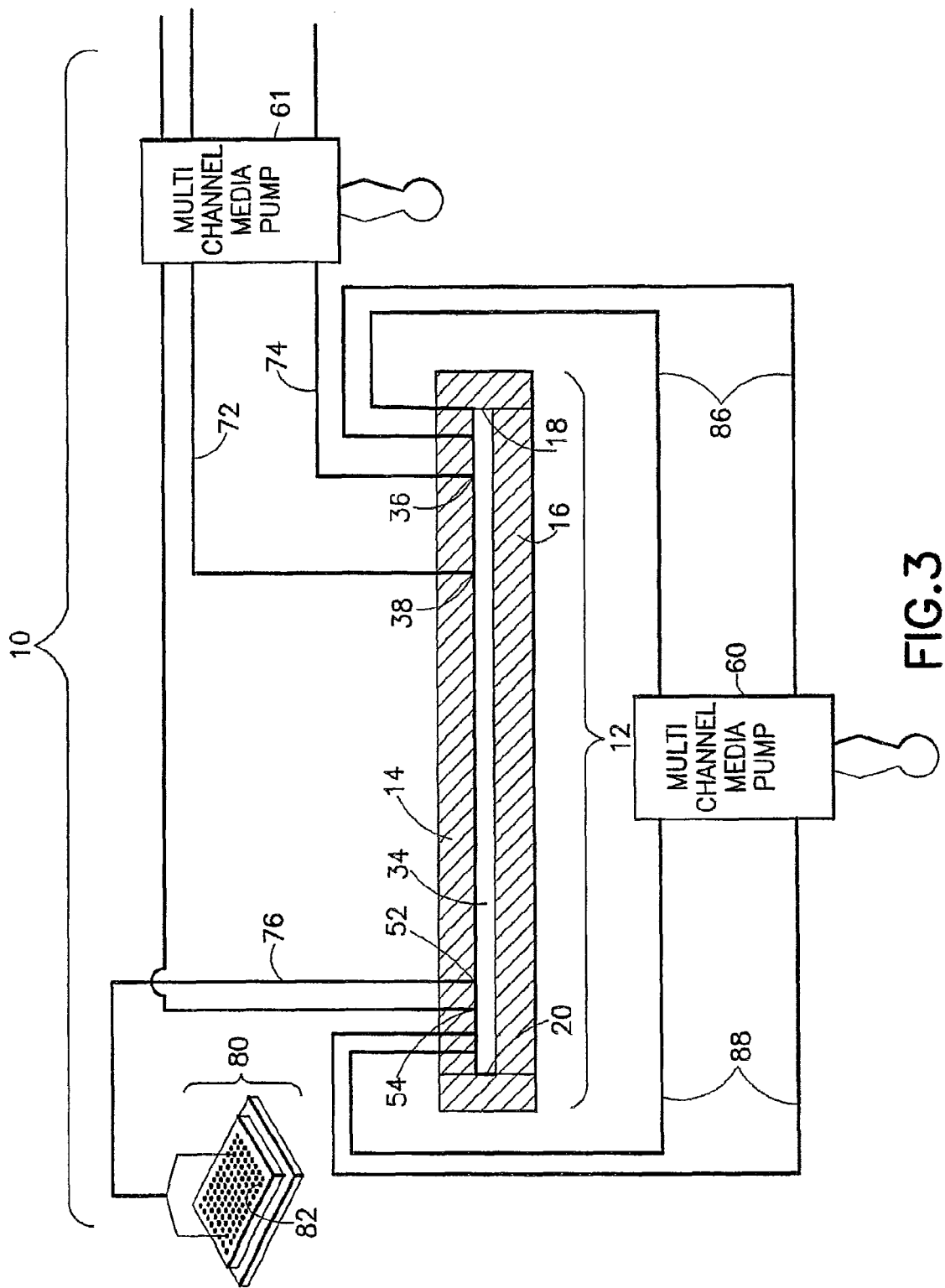
FIG. 3 describes an FFE apparatus suitable for carrying out free-flow electrophoresis according to an embodiment of the present invention.

The general method of the present invention is reflected in FIG. 2 (specifically FIGS. 2a-2e) while the elements typically required for carrying out the invention are collectively described in FIGS. 3, 4, 7a, and 8a. Reflected schematically in FIGS. 3 and 4 are two embodiments of an electrophoresis apparatus 10 including an electrophoresis chamber 12 as well as elements relating to and/or connected to the electrophoresis chamber 12, while FIGS. 7a and 8a reflect specifically the electrophoresis chamber 12 as well as the electrophoretic behavior of the particles as schematically represented in the electrophoresis chamber 12.

An apparatus 10 that may carry out aspects of the invention comprises all or a portion of the following elements:
an electrophoresis chamber 12,
separation media inlets 36,
sample inlet(s) 38,
electrodes (cathode 24 and anode 26),
a power supply (not shown),
a first fluidic displacement system 60,
a second fluidic displacement system 61,
controller(s) for controlling the power supply and/or the fluidic displacement systems.

Additionally, the following elements are typically desired to optimize the control, flexibility, and performance of embodiments of the invention:
cathode media 170,
anode media 172,
electrode/media spacer or barrier,
chamber spacer 22,
temperature controller 174,
cooling element 178,
sample outlets 52.

The above components and how they interrelate as a system will be described specifically herein below, but first the general method according to embodiments of the present invention is illustrated with reference to FIG. 2.

In the initial state shown on FIG. 2a, stage 0 begins with the sample and separation media introduced into the separation space of the electrophoresis chamber. No voltage or, optionally, an ineffective voltage is applied between the electrodes. In stage 0, there is an ineffective environment for successful electrophoretic migration to occur. This could be as a result of zero or an otherwise ineffective amount of electrophoretic field strength between the electrodes, or optionally due to rapidly introducing the sample and separation medium into the chamber thereby not providing enough residence time for effective electrophoretic migration to occur.

Stage 1 shown in FIG. 2b begins by reversing the flow rate of the combined sample and separation media in cycles of forward and reverse movement in no particular order. Preferably, during a portion of stage 1, an electrophoretic field is not causing electrophoretic migration to occur. The displacement of the sample particles of interest is generally less than the length of the electrodes. The voltage is increased or applied between the electrodes to thereby produce an effective field strength for electrophoretic migration to take place. Typical field strengths applied are in the range of about 250 V/cm, although the specific field strength used in a separation experiment will be dependent on a number of factors. Selecting an optimal voltage for cyclic FFE operation in a given FFE apparatus is well within the skills of the person skilled in the art.

The next stages 2 and 3 are shown in FIG. 2c. An effective electrophoretic field is causing the particles to electrophoretically migrate due to the voltage applied between the electrodes. It should be noted that in stages 2 and 3, the sample particles of interest are always in between and subjected to the electrophoretic field between the electrodes since the displacement of the sample and separation media sufficiently maintains the sample particles of interest to stay within the length of the electrodes.

It should be noted that during stages 2 and 3, the ability for the sample to electrophoretically migrate depends on the type of electrophoretic process employed by the user (i.e., isotachophoresis, isoelectric focusing, or zone electrophoresis), as well as the electrophoretic mobility of the sample in the separation media which is heavily influenced by the characteristics of the separation media chosen as well as the ability for current to flow between the electrodes. It should also be noted that stage 2 and stage 3 differ only in direction of flow of sample and separation media during electrophoretic migration, and can be repeated multiple times with similar or different flow characteristics. An example would be to move the sample and separation media during stage 2 with a certain average fluidic velocity and during stage 3, to move them backwards with an average fluidic velocity that is a fraction of or a multiple of the average fluidic velocity in stage 2.

When stages 2 and 3 are no longer performed, stage 4 may take place as shown in FIG. 2d. Essentially, stage 4 involves displacing the sample to be eluted towards sample outlets. While in FIGS. 2, 7a, and 8a the sample outlets are disposed at the opposite side of the electrophoresis chamber, in other embodiments, the sample outlets may be on the same side as the sample inlets and separation media inlets.

In FIG. 2d, stage 4 involves essentially minimal, preferably no electrophoretic migration of the sample during elution to the sample outlets. This can be accomplished by reducing or eliminating the electric field between the electrodes by lowering or removing the voltage between the electrodes. Optionally, this can be accomplished by quickly forcing the sample and separation media towards the sample outlets at an average fluid velocity that minimizes the duration and therefore the impact of an electrophoretic field on the migration of the particles or sample prior to reaching the sample outlets. It should be recognized that stage 4 is easiest performed by having no voltage applied during elution or extraction of the electrophoretically separated sample from the electrophoresis chamber 12. It will be appreciated that the above is particularly useful for zone electrophoresis FFE or isotachophoresis FFE applications. However, removing or reducing the voltage is not important when performing FFE in isoelectric focusing mode (IEF) since the total charge or net surface charge of the particles is zero at their final position between the electrodes with the consequence that no further migration is observed upon a continued application of an electric field.

Stage 4 as shown in FIG. 2d demonstrates elution of the sample and separation media, thereby enabling further analysis or processing of the eluted sample. Stage 5, shown in FIG. 2e which may occur in additional embodiments simultaneously with stage 4 (FIG. 2d) or at a time after stage 4 terminates, thereby enabling further electrophoretic separation to occur for additional samples or electrophoretic environments. While FIG. 2 demonstrates basic principles of embodiments of the present invention, other aspects of the invention will be shown throughout the application.

Finally, stage 5 is carried out as shown in FIG. 2e, essentially a repeat of stage 0 shown in FIG. 2a. Optionally, FIG. 2e may be avoided or abandoned if only one electrophoresis process is needed by the user. Alternatively, stage 5 can be combined with stage 4 as long as mixing of the new sample with the separated sample from the previous run is prevented.

Figure 9A:
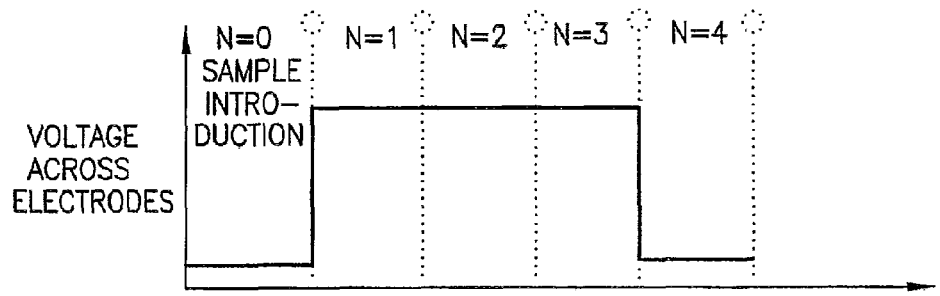
FIGS. 9A, 9B, and 9C depict voltage, media flow velocity, and media displacement, respectively.
Figure 9B:
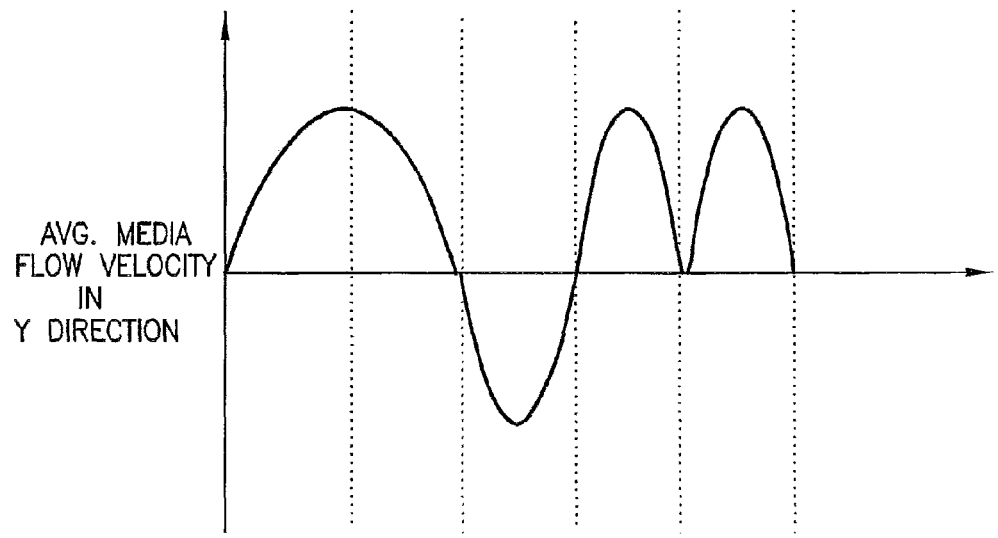
Figure 9C:
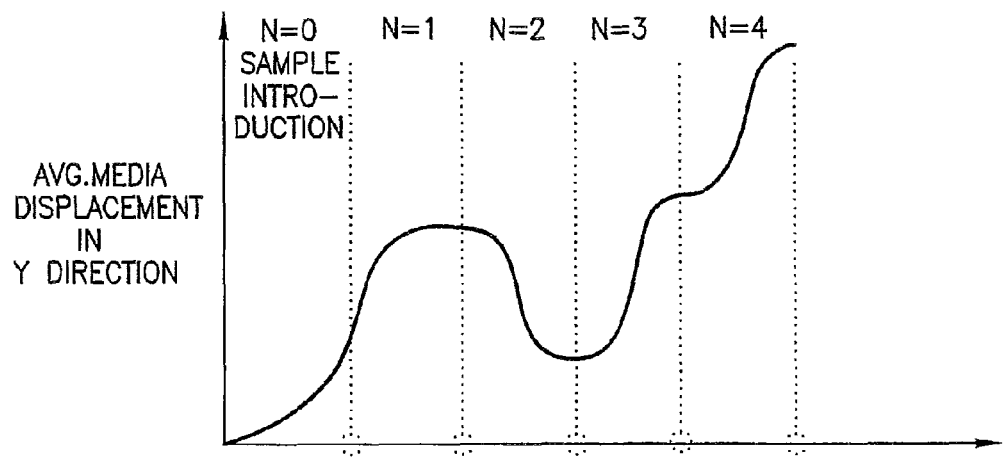
Figure 10A:
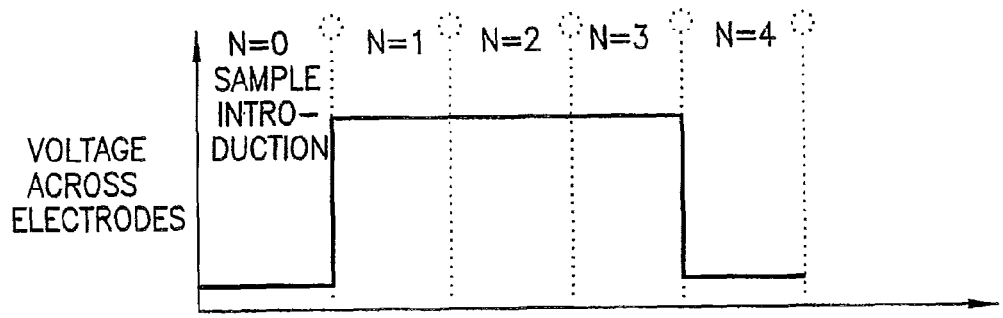
FIGS. 10A, 10B, and 10C depict voltage, media flow velocity, and media displacement, respectively.
Figure 10B:
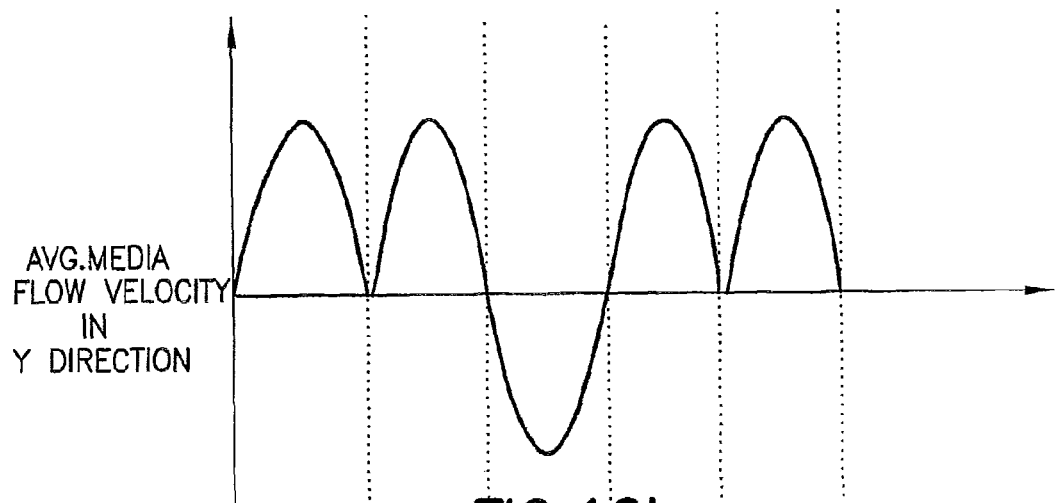
Figure 10C:
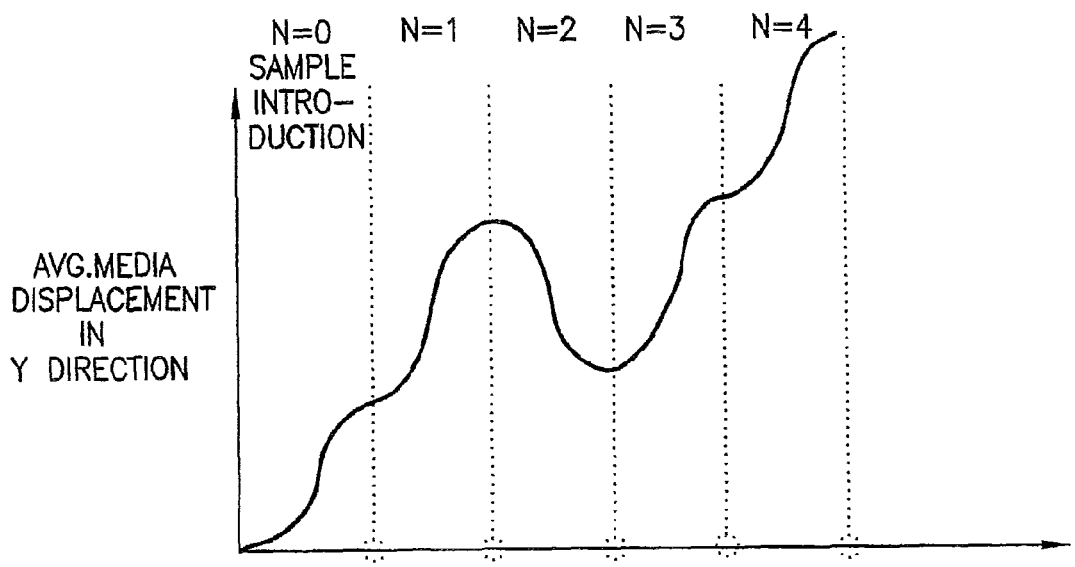
Figure 11A:
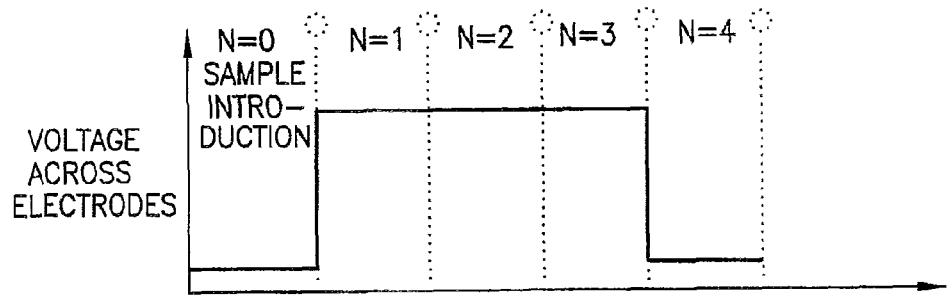
FIGS. 11A, 11B, and 11C depict voltage, media flow velocity, and media displacement, respectively.
Figure 11B:
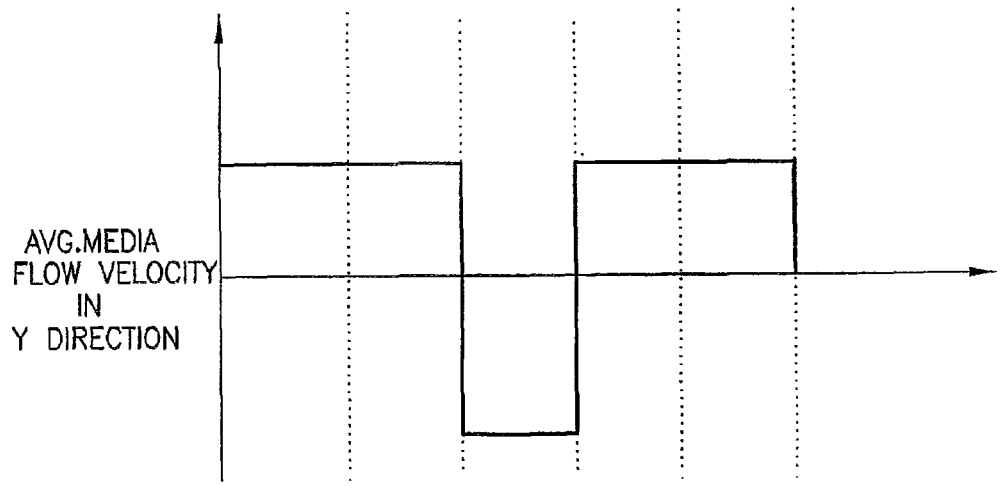
Figure 11C:
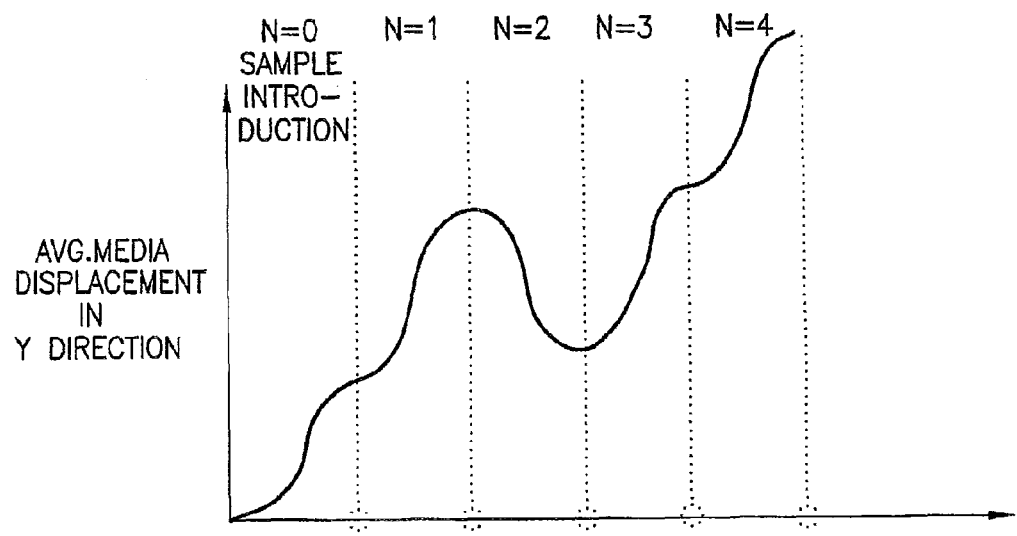

As shown in FIGS. 9, 10 and 11, different voltage, particle flow velocity, and particle displacement profiles may exist that correspond to a sample being subjected to steps or stages 0 through 4 of the embodiment as reflected in FIG. 2. For the purposes of FIGS. 9 to 11, the Y direction may correspond to the direction from the inlet end wall towards the outlet end wall. FIGS. 9 to 11 are similar in many regards, with exception to the acceleration and deceleration of the media flow velocity. In FIG. 9b, it is apparent that the method of the invention may be carried out by applying the voltage needed for electrophoretic migration to occur while the sample is moving forward (in this case, along the Y direction), while in FIG. 10b, the sample is brought to a stop prior to applying the voltage needed for electrophoretic migration. In FIG. 11, the reversal of the sample and separation media flow is instantaneous (e.g. when using peristaltic pumps where the direction of the pump is switched very fast, see FIG. 11b), although a slower and gentler reversal of the flow is certainly desirable to avoid any turbulences affecting the separation quality.

It should be noted that while FIGS. 9 to 11 are representative of certain embodiments of the invention, many other conditions of voltage, media and sample flow rate, and sample displacement are possible and can be appreciated by one skilled in the art. Additionally, the number of cycles able to be achieved for other embodiments of the invention may be altered, either decreased or increased, and can therefore provide the user with flexibility for carrying out free-flow electrophoresis in a cyclic interval mode of operation.

While FIG. 2 outlines the general mode of an embodiment of the invention and FIG. 2c outlines the general electrophoretic separation step of embodiments of the invention, it should be noted that each of the three primary electrophoresis processes may be employed (i.e., isotachophoresis, zone electrophoresis, and isoelectric focusing) as the electrophoretic separation step. This is shown in more detail schematically in FIGS. 7a and 8a for zone electrophoresis and isoelectric focusing, respectively.

During continuous operation, band widening comes about due to the laminar flow cross section, which results in higher retention times for the analyte in the electrical field, and hence a stronger lateral migration in the area of the electrophoresis chamber walls. This triggers an additional sickle-shaped band widening that is superposed over band widening via diffusion.

In contrast to the above, during cyclic interval operation where the electrical field acts on an analyte, band widening is caused solely through diffusion, and hence is lower than in cases of continuous operation. Lower band widening leads to a higher resolution. In other words, resolution is better in cyclic interval operation than in continuous operation (CFFE). Thus, the cyclic interval free-flow electrophoresis yields enhanced resolution of separation compared to continuous free-flow electrophoresis. Moreover, cyclic interval operation may achieve the same or better level of resolution when compared to static interval free-flow electrophoresis, yet in a much shorter time frame. This is due to the higher field strength that can be applied if the sample and separation media is in motion compared to the prior art interval FFE where the electromigration occurred statically (flow turned off).

In other embodiments of the invention, the method can be combined with other variations of free flow electrophoresis processes and devices. For example, multiple devices or set-ups can be used, which are then arranged in parallel and/or in series, for example as described in co-pending application US 2004/045826 to Weber. In such combinations, the other electrophoresis processes may be also carried out in the cyclic interval, static interval mode or continuous mode as described herein. By selecting the appropriate operation modes (cyclic interval, interval or continuous) and separation modes (ZE, IEF and/or ITP), powerful separations of a variety of different particles may be achieved.

As shown in FIGS. 3, 4, 7a and 8a, an electrophoresis apparatus 10 that may carry out aspects of the invention comprises an electrophoresis chamber 12 defined by a floor or bottom plate 16, a cover or top plate 14, end walls 18, 20 and side walls 56, 58. The end walls 18, 20 and side walls 56, 58 preferably form a substantially rectangular electrophoresis chamber 12 structure interposed and supporting the opposed parallel top and bottom plate (14 and 16).

A plurality of electrodes located in electrode spaces, i.e., cathode space 28 and anode space 30, are arranged proximate and parallel to the first and second side walls (56 and 58) within the electrophoresis chamber 12 so that the electrodes are generally parallel to one another. While it is not absolutely necessary that the electrodes are exactly parallel to each other, exact parallelism of the elongated electrodes is preferred in order to provide a homogenous electric field throughout the separation space within the electrophoresis chamber 12. Generally, an anode 26 is disposed in the anode space 30 and a cathode 24 is disposed in the cathode space 28. The electrodes (24 and 26) are typically separated from the electrophoresis chamber 12 by electrode spacers 32 which maintain a barrier to prevent electrophoretically separated particles from reaching, fouling, or otherwise interfering with the electrodes during operation. Typically, the electrode spacers 32 are constructed in the form of membrane electrode spacers 48 that are essentially filter membranes preventing exchange of media caused by hydro-dynamic flow. The membranes are typically located very close to the electrodes, but for clarity the drawings show the membranes spaced from the electrodes. A more detailed depiction of the above can be found in FIGS. 7a and 8a. The cross-sectional views shown in FIGS. 3 and 4 depict a cross-section cut through the electrophoresis chamber 12 in a direction shared by the electrodes, generally normal to the top plate 14 and bottom plate 16 as well as the inlet end wall 18 near the separation media inlets 36 which are described below.

A separation space or zone 34 is generally defined or delimited as the space between the electrode spaces (28 and 30) and top and bottom plate (14 and 16) not including the electrode spacers 32. The separation space 34 is flanked by the anode 26 and the cathode 24 which generate an electric field when connected to a power supply (not shown). Preferably, the direction of the electric field is substantially parallel to the top and bottom plate (14 and 16), and is preferably also substantially perpendicular to the direction of the displacement of the bulk separation medium within the electrophoresis chamber 12.

Preferably, the top and bottom plate (14 and 16) are stationary with respect to the electrodes and each other, at least when voltage is applied to the electrodes, so that the forces caused by the displacement flow and the electric field act on the sample and the ions in the separation medium only.

Typically, the power supply is a direct current (DC) power supply with an AC to DC converter supplying current between the electrodes in a generally controlled manner. Additionally, a controller may exist to control the flow of current between the cathode 24 and anode 26.

The electrodes (cathode 24 and anode 26) are typically composed of a metal such as platinum that will not easily be oxidized in the electric field. The electrodes (24 and 26) are optionally washed constantly by a salt or buffer solution to remove electrolysis products that are created during the process. The solution or media herein is generally referred to as cathode media 170 and anode media 172.

The bottom plate 16 and the top plate 14 of the electrophoresis chamber 12 can independently be made of glass (preferably polymer-coated glass), or suitable plastics, such as PVC, polycarbonate, Plexiglas, polyhalohydrocarbons, or Lucite® (an acrylic resin consisting essentially of polymerized methyl methacrylate).

The top and bottom plate (14 and 16) are typically separated by chamber spacers 22 (not shown) that act as gaskets or seals. The chamber spacers 22 usually delimit the separation space 34 within the electrophoresis chamber 12. The separation space 34 (space between plates) usually has a thickness of about 0.01 to about 1.5 mm, preferably of about 0.05 to about 1 mm and most preferably of about 0.1 to about 0.5 mm. It will be appreciated that the thickness of the separation space depends on many factors, including the size of the electrophoresis chamber 12 and the sample volume to be separated or detected and may be adapted accordingly by those skilled in the art.

Figure 7A:
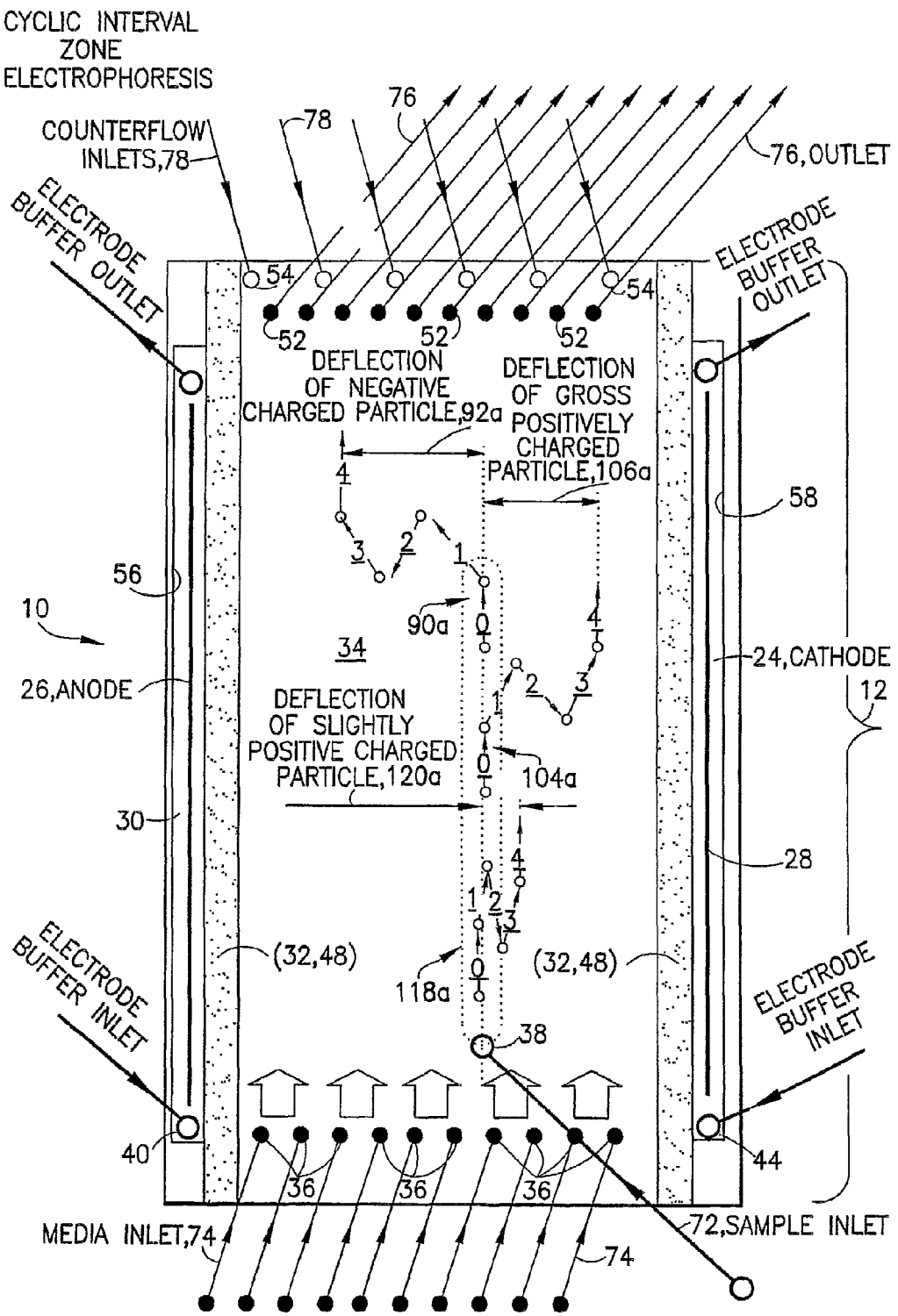
FIG. 7 illustrates anion and cation migration for the zone electrophoresis mode of an embodiment of the present invention.
Figure 8A:
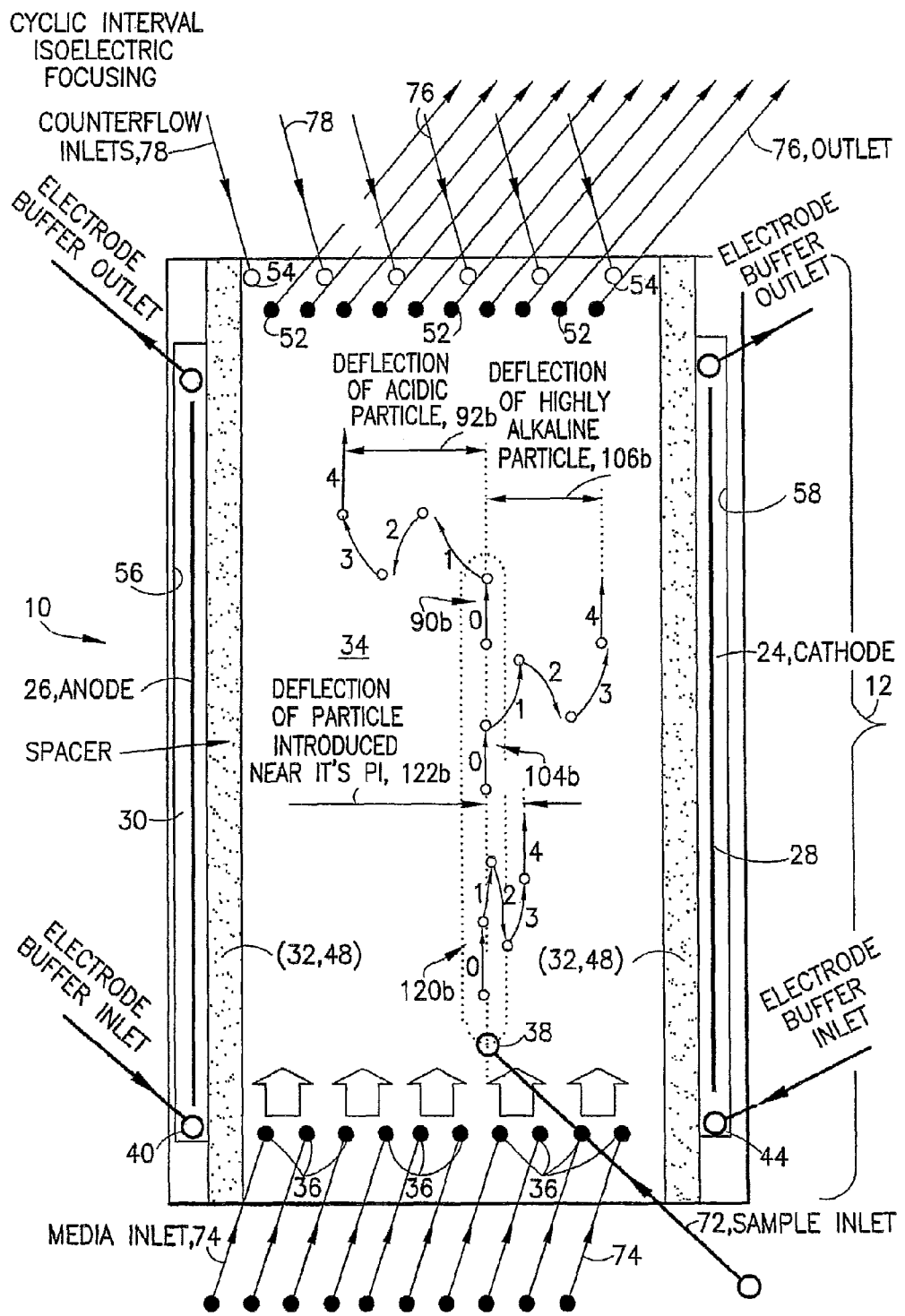
FIG. 8 illustrates migration of particles of various isoelectric points (PI) for the isoelectric focusing mode of an embodiment of the present invention.

An apparatus 10 according to embodiments of the present invention comprises elements to help introduce and extract the sample and separation media into and from the electrophoresis chamber 12. Integral to the electrophoresis chamber 12 at its lower end wall are, for example, a plurality of separation media inlets 36, typically having ports (not shown) which are connected by conduits as separation media inlet tubing 74, such as flexible TEFLON tubes. The tubes are in fluidic communication to feed channels of a fluidic displacement system 60 (e.g., a multi-channel pump such as a peristaltic pump). The separation media inlets are generally arranged collinear at the lower end of the electrophoresis chamber 12 and equidistant with respect to the corresponding outlets, as illustrated, e.g. in FIGS. 7a and 8a. Sample inlet tubing 72 conduits for introducing and eluting or expelling the sample and related media and buffers into and out from the electrophoresis chamber 12 are shown in FIGS. 7a and 8a and are schematically shown in FIGS. 3 and 4. The separation media inlets 36 are supplied with a separation medium while the electrode inlets (40 and 44) are fluidically connected to the electrode spaces (28 and 30) and supplied with the electrode stabilization medium for the anode 26 and cathode 24. The sample containing the analytes is injected into a predetermined position within the separation space 34 through sample inlet 38. Wherein multiple separations are capable of being performed simultaneously and parallel to each other between one or more pairs of electrodes or conductivity walls, it is contemplated that multiple sample inlets 38 can be used simultaneously to introduce the correct sample or samples into the separation space 34. In this case, the multiple sample inlets are also positioned collinear and equidistant to the outlet end as described above for embodiments comprising multiple separation media inlets.

Alternatively, the separation media inlets 36 and sample inlets 38 can be combined. In this embodiment, the sample may be introduced through the separation inlets, for example injecting the sample through an inlet port in the portion of the tubing 74 external to the electrophoresis chamber 12.

An apparatus 10 according to embodiments of the present invention may comprise as many as three fluidic displacement systems. A first fluidic displacement system controls the displacement of the sample and separation media in the separation space 34 as will be described in detail below. Typically, the first fluidic displacement system is a multi-channel peristaltic pump but may take on the form of other pumps sufficient to displace fluid in a controlled manner within the separation space 34.

A second fluidic displacement system serves two purposes, namely the introduction of the sample into the separation space 34 and the introduction and displacement of the separation media into and within the separation space 34. The second fluidic displacement system comprises two multi-channel peristaltic pumps, one for the introduction of the sample into the separation space 34 and one for the introduction and displacement of the separation media and the sample. It however is possible to have one multi-channel peristaltic pump perform both tasks. The use of multi-channel peristaltic pumps is preferred, but the second fluidic displacement system may take on the form of other pumps sufficient to displace fluid in a controlled manner within the separation space 34.

The second fluidic displacement system may also perform the task of introducing and displacing a counterflow media into and within the separation space 34 as will be described below in detail. It however is also contemplated to use a further multi-channel pump for this purpose.

Finally, a third fluidic displacement system (not shown) may be utilized for circulating the electrode media within the electrode spaces.

The fluid displacement systems interface with the various types of media in a controlled fashion. A controller (not shown in the figures) is typically utilized to manage the flow rates and pressures of the above fluids to carry out the desired separation or fractionation protocol chosen by the user.

In an embodiment of an apparatus capable of carrying out the invention shown in FIG. 3, two fluid displacement systems 60 and 61 or pumps are utilized. A first fluidic displacement system 60 is utilized to provide bulk fluid displacement of the sample and separation media between the electrodes along the direction of the electrodes. A second fluidic displacement system 61 is used to introduce the sample and separation media into the separation space 34, either together or separately, and to initially displace both within the separation space 34. In a preferred embodiment, the second fluidic displacement system 61 comprises two fluidic displacement units, one for the introduction of the sample into the separation space and one for the introduction and displacement of the separation media. This second fluidic displacement system 61 is also used to remove or elute the sample after electrophoretic separation from the separation space 34 through sample outlets 52. Separate valving may be utilized to enable or prevent the introduction of the sample through sample inlet 38 into the separation space as desired by the intended operation of embodiments of the invention.

An inlet end cycle conduit 86 and an outlet end cycle conduit 88 are operatively connected to the first fluidic displacement system 60 and are additionally fluidically coupled to the separation space 34 of the electrophoresis chamber 12. Their use is related to cycling of the separation media and samples back and forth along the direction of the electrodes rather than introduction of the separation and sample media into the separation space 34.

The first fluidic displacement system 60 provides a displacement force or pressure for controlling the bulk fluid flow of sample and separation media after they have been introduced into separation space 34. For example, once separation space 34 and the inlet and outlet cycle tubes are filled with media or a buffer solution, operation of the first fluidic displacement system 60 (in this case, a peristaltic pump), transfers the sample and separation media towards one end of the electrophoresis chamber 12, and reversing the operation of the first fluidic displacement system 60 causes the sample and separation media to move towards the other end of the electrophoresis chamber 12. Desirably, the operation of the first fluidic displacement system 60 will be reversed prior to the sample reaching either end of the separation space 34. More desirably, the operation of the first fluidic displacement system 60 will ensure that the sample does not leave that portion of the separation space 34 that is between the electrodes.

The second fluidic displacement system 61 (e.g. in the form of two peristaltic pumps) is connected via sample inlet tubing 72 to the sample inlet 38. Also connected to the second fluidic displacement system 61 is separation media inlet tube 74 that is fluidically coupled to separation media inlet 36. The second fluidic displacement system 61 controls the delivery of sample and separation media into the separation space 34 as well as controls the extraction of fractionated sample from the electrophoresis chamber 12 into individual collection wells, vessels or cavities 82 in for instance a microtiter plate 80.

It should be noted that desirably, when second fluid displacement system 61 is in operation, first fluidic displacement system 60 is not and vice versa.

In operation, the embodiment reflected in FIG. 3 is operated as follows. The second fluidic displacement system 61 causes the introduction of the sample and the introduction of the separation media into the separation space 34 as well as the advancement of both the sample and the separation media into the center region of the displacement space 34. Preferably, electrophoretic migration does not occur during this stage. Next, the first fluidic displacement system 60 moves the sample and separation media back and forth along the direction of the electrodes by displacing fluid through the inlet end cycle conduit 86 and the outlet end cycle conduit 88. During a portion of this movement or cycling, an electrical current flows between the electrodes thereby causing or enabling electrophoretic migration. After sufficient cycling and electrophoretic migration, the first fluidic displacement system 60 preferable is no longer used or is turned off, and the second fluidic displacement system 61 causes additional separation media to be introduced into the separation space thereby displacing the separated sample from the separation space, through sample outlets and into preferably collection vessels such as those found in a microtiter plate. It may be possible during this elution phase to also introduce additional sample into the separation space.

Also, it may be possible to introduce counterflow media into the outlet end wall 20 through counterflow inlets 54, wherein the sample outlets 52 are generally interposed between the sample media inlets 38 and the counterflow inlets 54. During the elution phase or step, it is desirable that the high voltage is off or at least ineffective to cause electrophoretic migration, particularly for the ITP and ZE operation modes. For obvious reasons, turning off the voltage is not necessary when the separation is carried out in IEF mode (see below). It should be noted that valving of the inlets, outlets, or tubing conduits involved in this embodiment may facilitate the process steps as described above.

In an additional embodiment of an apparatus capable of carrying out the invention, one fluidic displacement system 62 is utilized for controlling the movement of fluids to carry out electrophoretic separation in a cyclical interval manner. A first pump of the fluidic displacement system 62 is connected via sample inlet tubing 72 to the sample inlet 38. A second pump of the fluidic displacement system 62 is connected to the separation media inlet tube 74 that is fluidically coupled to separation media inlet 36. The fluidic displacement system 62 controls the delivery of sample and separation media into the separation space 34 as well as the movement of fluids by providing a displacement force or pressure for controlling the bulk fluid flow of sample and separation media after they have been introduced into separation space 34. For example, once separation space 34 and the inlet and outlet cycle tubes are filled with media or a buffer solution, operation of the fluidic displacement system 62 (in this case, a peristaltic pump), transfers the sample and separation media towards one end of the electrophoresis chamber 12, and reversing the operation of the fluidic displacement system 62 causes the sample and separation media to move towards the other end of the electrophoresis chamber 12. Desirably, the operation of the fluidic displacement system 62 will be reversed prior to the sample reaching either end of the separation space 34. More desirably, the operation of the fluidic displacement system 62 will ensure that the sample does not leave that portion of the separation space 34 that is between the electrodes.

After electrophoretic separation has occurred, the net flow of sample into and out of the separation space 34 is held constant by maintaining the volumetric flow of media introduced by the counterflow inlets 54 and the separation media inlets 36 to each be zero or positive, wherein when the sum of both of the flows is positive, the fractionated sample is capable of eluting through the sample outlets 52, through the outlet tubing 76 and into preferably individual collection vessels or cavities 82 disposed in, for instance, a microtiter plate 80.

Optionally the second pump of the fluidic displacement system 62 may also be connected to a counterflow tubing 78 fluidically coupled via a counterflow inlet 54 into the separation space 34.

In addition to the separation media inlet tubing 74, separate valving may be utilized to enable or prevent the introduction of the sample through sample inlet 38 into the separation space 34 as desired by the intended operation of embodiments of the invention.

The embodiment depicted in FIGS. 4a and 4b operates as follows. The fluidic displacement system 62 causes the introduction of the sample and separation media into the separation space 34. In a preferred embodiment, the fluidic displacement system 62 comprises two fluidic displacement systems, one for the introduction of the sample into the separation space and one for the introduction and displacement of the separation media. Preferably, electrophoretic migration does not occur during this stage. Next, the fluidic displacement system 62 moves the sample and separation media back and forth along the direction of the electrodes. This is performed such that operation of fluid displacement system 62 causes the separation media and the sample to shift forward and backward, towards and away from the inlet end wall 18 in a cycling motion. In variations of the embodiment depicted in FIGS. 4a and 4b, both the counterflow tubing 78 and separation media inlet tubing 74 are engaged with fluidic displacement system 62 to cause pressure differentials between the counterflow inlets 54 and the separation media inlets 36.

During a portion of the movement or cycling, an electrical current flowing between the electrodes causes or enables electrophoretic migration. After sufficient cycling, electrophoretic migration or both, the fluidic displacement system 62 is used to elute the separated sample from the separation space 34 through sample outlets 52 and into preferably collection vessels or cavities 82 such as those found in a microtiter plate 80. It may be possible during this elution phase to also introduce additional sample into the separation space.

Also, it may be possible to introduce counterflow media near the outlet end wall 20, wherein the sample outlets 52 are generally interposed between the sample media inlets 38 and the counterflow inlets 54. During the elution phase or step, it is desirable that the high voltage is off or at least ineffective to cause electrophoretic migration at this point. It should be noted that valving of the inlets, outlets, or tubing conduits involved in this and other embodiments may facilitate the process steps as described above.

During the cycling of the sample flow, it is essential by any means to prevent the entry of sample or media into the sample outlet as well as the entry of air into any of the inlet tubing. For example, in the embodiment depicted in FIGS. 4a and 4b, it is desirable to have the sample outlets resist or prevent the entry of sample or media into the outlets during cycling of the sample flow by closing a valve, causing a pressure head to develop in the outlets by elevating the outlet tubing 76 with respect to the separation space 34, or constricting the outlet tubing such that there is more fluidic resistance for the separation media to enter the outlet tubing 76 than that of the counterflow tubing 78, sample inlet tubing 72, or separation media tubing 74. Other means of accomplishing the same are to be understood by one skilled in the art.

An apparatus 10 according to embodiments of the present invention may further contain a fraction collector outlet or sample outlet 52 and outlet tubing 76. In most cases of operation, typically after electrophoretic separation according to at least one of the above mentioned electrophoresis modes, the separated fractions, i.e., analytes of interest, are collected through the spatially distinct sample outlets 52 arranged in a line and in proximity to an outlet end wall 20, typically opposite an inlet end wall 18 adjacent to the separation media inlets 36. The analytes or fractions are led through outlet tubing 76 or conduits to individual collection vessels of any suitable type, preferably cavities 82 or wells in microtiter plates 80 (see FIGS. 3 and 4). In the collection vessels, the analytes are collected together with the separation medium and, optionally, the counter-flow medium. The distance between the individual sample outlets 52 of the array of collection outlets should generally be as small as possible in order to provide for a suitable fractionation/separation. The distance between individual sample outlets 52, measured from the centers of the collection outlets, is typically from about 0.1 mm to about 2 mm, more typically from about 0.3 mm to about 1.5 mm, and is almost always dependent on the maximum diameter of the outlet tubing 76. This series of tubing openings with the smallest possible distance between the openings is referred to as a fractionating device, and the number of these outlet tubes arranged in parallel ranges is between 2 and a maximum of 1000, preferably between 30 and 200, and more preferably between 20 and 100. The number, shape, and location of these outlets may be modified in different modes to purposefully fractionate or isolate a particular portion of the separated sample according to a separation gradient.

The selected sample components or fractions collected may be used for analytic or preparative purposes. Alternatively, the fractions may be directly or indirectly introduced into the same or optionally a remote electrophoretic device to carry out additional processing. Such may occur in the event of performing a coarse fractionation followed by a fine (higher resolution) fractionation, or in one or multiple electrophoretic modes (ZE, IEF, ITP, or combinations thereof).

Extraneous sample components that are not collected through the collection outlets through which the desired sample is withdrawn or which are collected through different collection outlets can also be discarded.

In various embodiments of the invention, the separated sample may be intentionally diluted during the fractionation step or alternatively, may be extracted from the chamber by use of a counterflow process. In the counterflow process, a counterflow medium 176 may be introduced through counterflow inlets 54 generally opposing the direction of bulk flow of sample during elution, for the sample and separation media in the separation space 34 to be selectively extracted from the separation space 34. The sample and separation media unite with the counterflow media at the extraction or sample outlets 52, and are extracted therethrough. The counterflow serves to enhance resolution of separation by allowing adjustment and control of the flow and pressure conditions at the collection outlets, thereby maintaining control for the desired fraction to reach and be extracted through the desired sample outlet 52. Details of the counterflow process are disclosed, e.g., in U.S. Pat. No. 5,275,706 to Weber. In view of the above-mentioned advantages, using a counterflow is generally preferred, although in certain situations, such counterflow may not be desired, e.g., due to the inherent dilution effect.

Figure 4A:
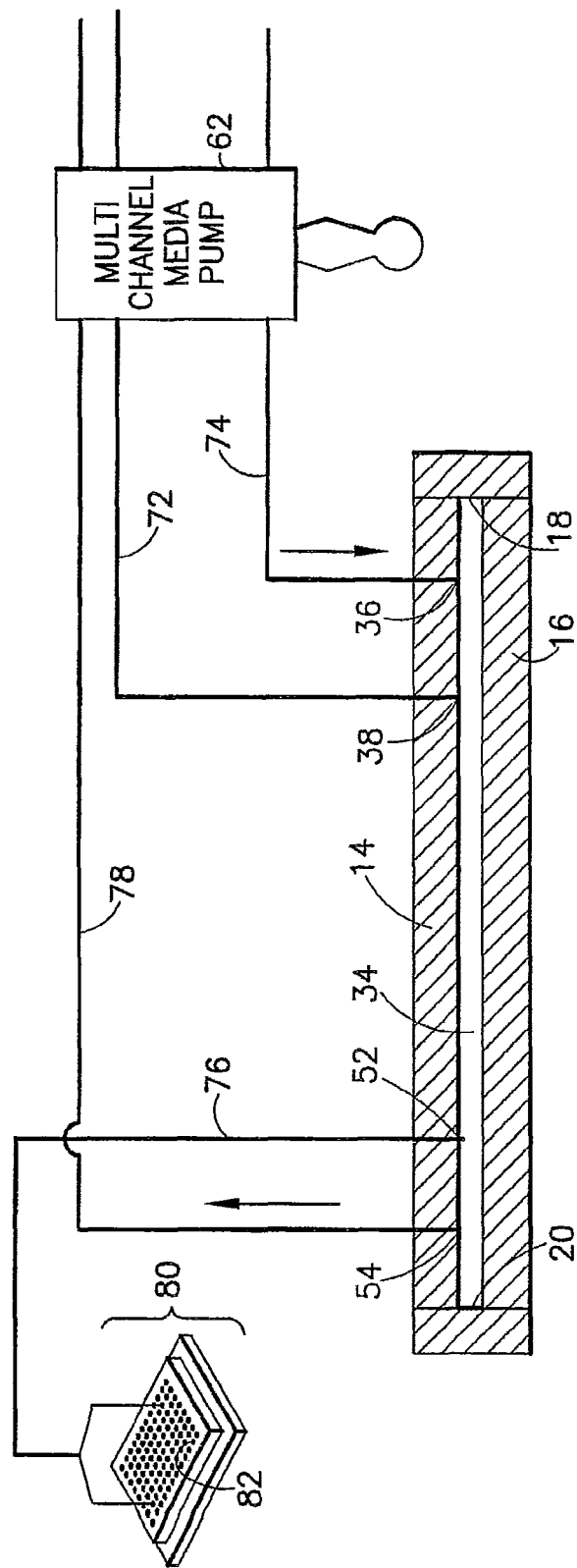
FIGS. 4a and 4b describe another setup embodiment suitable for carrying out free-flow electrophoresis according to an embodiment of the present invention.
Figure 4B:
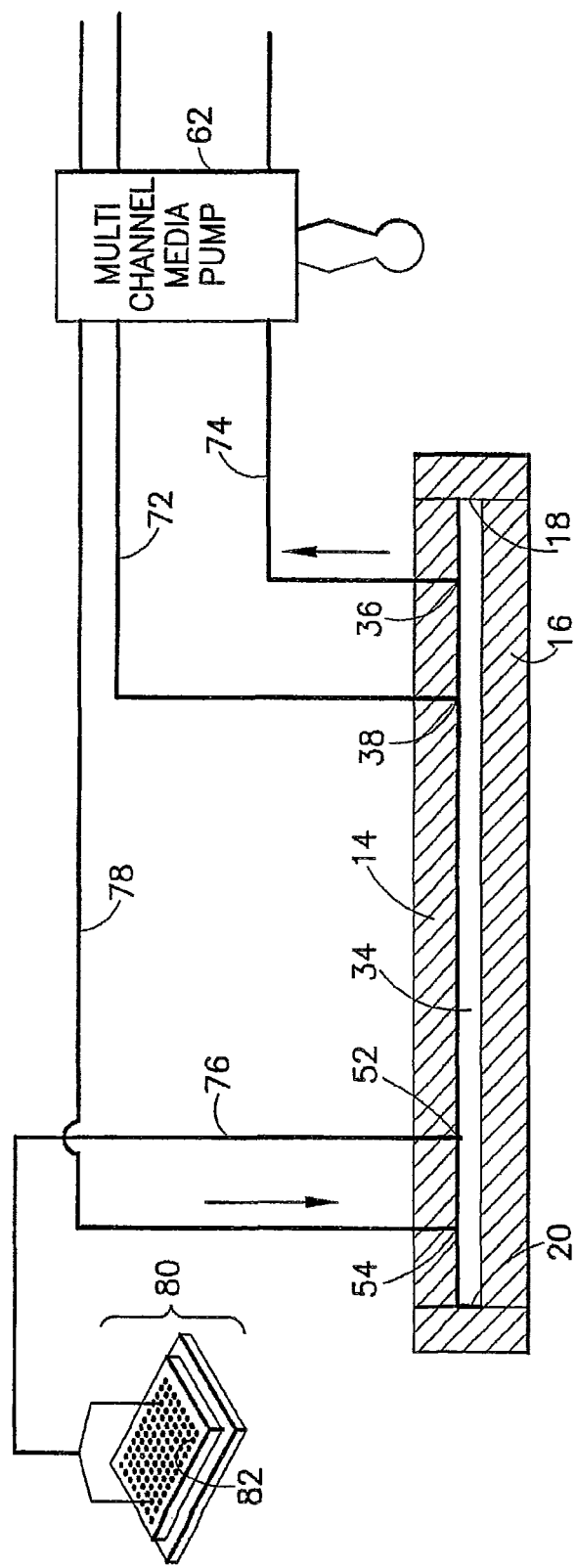
Figure 6:
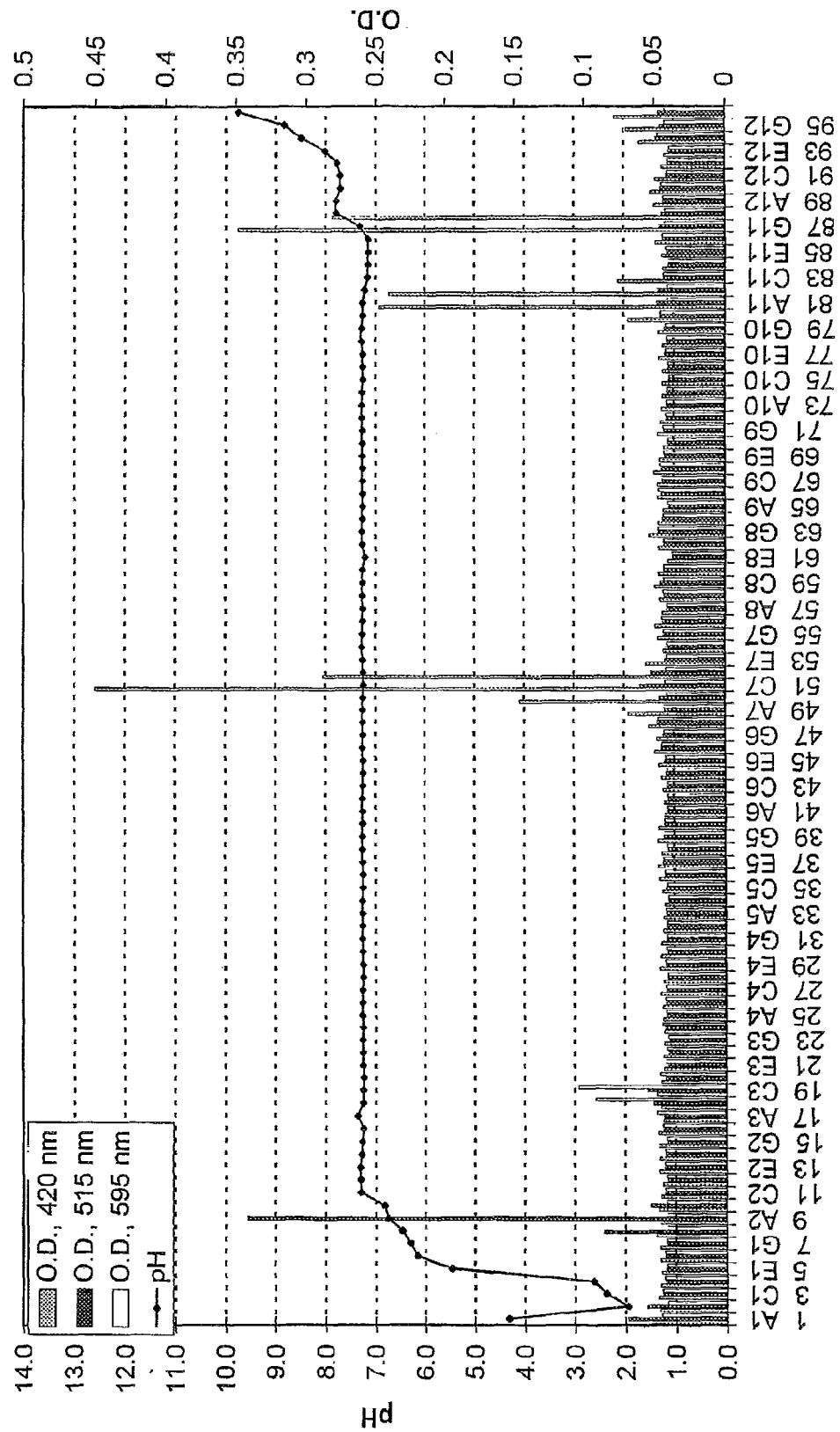
FIG. 6 demonstrates performance results of the cyclic FFE method according to an embodiment of the present invention.

In addition to the use of counterflow depicted in FIGS. 4a and 4b described above, it is possible to use a counterflow technique in the electrophoresis chamber 12 according to an embodiment of the invention during sample elution. For example, in FIGS. 7a and 8a, a counterflow medium may be introduced during an elution step where the sample has been subjected to electrophoretic migration in the electrophoresis chamber 12 via counterflow tubing 78 towards and through counterflow inlets 54. The counterflow medium is introduced in a direction opposite the direction in which the sample and separation medium is eluted from the electrophoresis chamber 12. The counterflow enhances separation by allowing adjustment and control of the flow and pressure conditions at the sample outlets 52 and reduces the occurrence of any voids that may impact sample resolution during elution. For details of how to use counterflow, reference is again made to U.S. Pat. No. 5,275,706 which is incorporated herein by reference in its entirety.

The counterflow media, if used, are typically selected to be capable of modifying or surpassing the buffering capacity of the separation medium approaching the sample outlets 52, and may therefore be a material having the same physical properties such as viscosity and density but differing in conductivity and/or pH-value and/or their chemical ingredients. Typical counterflow and separation media are selected from the same group of media, and may contain components such as urea, glycerol, carbohydrates, and similar compounds.

A useful ratio of the flow rate of the separation medium to the flow rate of the counterflow medium is about 1:10 to about 10:1, more typically about 1:3 to about 3:1. The actual flow rates for the separation medium and the counterflow media depend on a variety of considerations, including the geometrical dimensions of the apparatus 10, the particular separation mode used (which may vary in required transit time), the sample to be separated, the separation medium used and the counterflow medium or media used in order to obtain an optimum separation of the analytes. Typical flow rates of all media into the system (stabilization and counterflow) may therefore range widely from 0.3 mL/hour to 3000 ml/hour, depending on the circumstances and the geometry of the electrophoretic chamber. The linear velocity of the sample and separation medium is, however, generally between 0.01 and 50 mm/sec, and preferably between 0.1 and 10 mm/sec.

Temperature control is also useful in the embodiments of the present invention. When current passes through an electrolyte solution, the temperature of the conduction medium increases, according to the phenomenon known as Joule heating which may influence viscosity and/or fluid flow through the chamber, thereby causing flow disturbances. To reduce disturbances affecting the laminar flow profile of the flowing medium caused by such heating, it is generally desirable to dissipate the Joule heat to the surroundings. Many ways to practically achieve the desired cooling will be apparent to the person skilled in the art. For example, a cooling element 178 (not shown) may be utilized to carry out such an effect. The electrophoresis chamber 12 may be arranged with its bottom plate 16 on a metal support that contains fluid flow channels connected to the cooling element 178. The cooling element 178 may be a temperature control device 174, such as a Peltier or thermoelectric (TE) module. A thermostat closed loop control system for measuring and controlling the temperature of the electrophoresis chamber 12 is useful to maintain the desired temperatures for the separation space 34. Useful temperature ranges are from about 2° C. to about 35° C., more typically from about 5° C. to room temperature (about 20-25° C.).

In embodiments of the invention wherein a membrane electrode spacer 48 isolates the cathode and anode spaces (28 and 30) from the separation space 34, the electrode spaces (28 and 30) may be purged by circulating a flow of cathode media 170 and anode media 172 (together referred to as electrode media) at a high flow rate using a pump. The electrode media may be cooled and reintroduced into the electrode spaces (28 or 30) in a continuous manner. How the electrode media is cooled is reflected in FIGS. 7a and 8a, wherein the cathode media enters into the cathode media inlet 44 and exits via the cathode media outlet 46. Before the cathode media or anode media re-enter the electrophoresis chamber 12, they may be subjected to a cooling element 178 such as a heat-transfer element that removes thermal energy from the anode and cathode media prior to reintroduction.

Specifically, as reflected in FIGS. 7a and 8a, the anode media 172 enters into the anode media inlet 40 and exits via the anode media outlet 42. In embodiments wherein the electrode spacer 32 is a physical barrier such as membrane electrode spacer 48, the flow rate of the cathode and anode media (170 and 172) can vary from the flow rate of the bulk sample and separation media.

It is readily apparent that other suitable ways for cooling the electrode media exist and can be applied by the person skilled in the art.

The controllers mentioned above for the power supply and fluidic control may operate as one unit, or optionally as independent units. Each may be controlled by the user independently of one another. Setting up the parameters of the protocol(s) processed in the controller(s), such as mode of electrophoresis, number of cycles, retention time of a cycle, etc., is preferably done by means of a software program providing a graphical user interface for entering the parameter values.

Accordingly, in another aspect, the present invention relates to a computer executable software code stored on a computer readable medium, wherein the code is suitable for effectuating the separation of particles in an electrophoresis chamber 12, wherein the electrophoresis chamber has a top plate, a bottom plate, and a plurality of electrodes generally parallel to one another with a separation space disposed therebetween, and one or more fluidic displacement systems for conveying a separation medium between the electrodes, wherein the software comprises code to enable selection and application of a voltage between the electrodes effective to manipulate particles by electrophoresis, code to enable displacement of at least a portion of the separation medium and sample toward a first direction parallel to the direction of the electrodes, and code to enable displacement of at least a portion of the separation medium and sample toward a second direction opposite the first direction; and code to enable displacement of the at least a portion of the separation medium and sample toward the first direction. In other words, the software program supports a user in selecting adequate parameter values for the intended separation process, including voltage, current, flow rates of separation medium, sample, and optionally counterflow medium as well as the number of cycles. This is typically accomplished by providing the user with forms to be filled in, which adapt their layout, e.g., the information and input fields shown, to the parameter values entered so far, i.e., selected mode of electrophoresis, etc. Additionally, the software program may verify the entered parameter values and inform the user about parameter values being incorrect or out of range. Furthermore, the software program may support the user by automatically providing parameter values, which can be derived from already established parameter values, e.g., total retention time after having entered the number of cycles and the retention time for each cycle.

Desirably, all media flow through the separation space 34 is done so under laminar flow conditions. As shown in FIGS. 3, 4, 7*a*, and 8*a*, the direction of flow from the various inlets (36 and 38) while filling the electrophoresis chamber 12 with the sample or with the separation media is shown by arrows for various embodiments of this invention.

Different modes of electrophoresis may be employed to influence particle migration based upon, for example, the particle's isoelectric point (i.e., isoelectric focusing of zwitterions (IEF)), or optionally based on the particles net charge (i.e., zone electrophoresis (ZE) for particles with different or varying net charges). Particles can also be separated based upon their electrophoretic mobilities when interposed between leader (fast moving) and trailing (slow moving) buffer systems (i.e., isotachophoresis (ITP) for anionic or cationic particles).

In a first mode of electrophoretic separation, a zone electrophoresis (ZE) FFE separation technique is carried out. Zone electrophoresis is based on the difference between the electrophoretic mobility value of the particles to be separated and that of the separation medium employed. FFE zone electrophoresis makes it possible to isolate analytes and particles on the basis of differing size and/or form and/or net surface charge.

The ZE FFE method is particularly suitable for separating "sensitive" bioparticles and complexes when specific demands have to be placed upon the separation medium during separation. This is typically the case when the biological function and integrity of the particles has to be maintained following separation. The special requirements in these cases are, e.g., a very restricted pH range for the separation medium, good separation medium buffer capacity, physiological compatibility of the buffer substances used, and a minimum content of various "essential" cations and anions, etc.

FIG. 7*b* shows a zone electrophoresis apparatus 10 with a flat pH profile 134. A separation medium flows in a laminar manner between both the electrodes as demonstrated within stage 2 and 3 of FIG. 2*c*. A sample with three groups of particles (90*a*, 104*a*, and 118*a*) to be separated is introduced into the separation medium via the sample inlet 38 and transported by the laminar flow of the separation medium. The three groups of particles are separated during stage 2 and 3 of the step as reflected in FIG. 2*c*, and are thereby allowed to migrate and be collected in distinct fractions in the pH gradient resulting from the electrical field generated between the electrodes in the separation medium as is indicated in FIG. 2*d*. Specifically, the paths of first particle 90*a*, second particle 104*a*, and third particle 118*a* are reflected in FIG. 7*a*. Each particle (90*a*, 104*a*, 118*a*) follows a special path or movement within stages 2 and 3 of electrophoretic migration. The particles have a net charge that influences their movement within the separation space under conditions that enable electrophoretic migration within the separation media. Third particle 118*a* has a slightly positive net charge and therefore under zone electrophoresis conditions, slightly deflects towards the cathode while the bulk fluid flow of the separation media influences net particle movement of third particle 118*a* with respect to the inlet and outlet ends of the chamber. Second particle 104*a* on the other hand has a relatively strong positive charge, and therefore during the path of movement under zone electrophoresis conditions, greatly deflects towards the cathode while the bulk fluid flow of the separation media influences net particle movement of second particle 104*a* with respect to the inlet and outlet ends of the chamber. First particle 90*a* on the other hand has a relatively strong negative charge, and therefore during the path of movement under zone electrophoresis conditions, greatly deflects towards the anode while the bulk fluid flow of the separation media influences net particle movement of first particle 90*a* with respect to the inlet and outlet ends of the chamber. It should be noted that FIG. 7*a* reflects a zone electrophoresis (ZE) separation wherein the particles will continue to migrate towards the electrode that has an opposite charge than the net charge of each respective particle in the presence of an electrophoretic field. If more cycles of forward and backward movement occurred, or if a longer period or duration of electrophoretic migration was allowed to take place, the particles would continue to migrate until they reached the electrode or some other electrode spacer 32 such as a membrane electrode spacer 48 or optionally a non-membrane electrode spacer 50 such as a high conductivity wall or buffer. In all cases of the first, second, and third particles (90*a*, 104*a*, 118*a*) the fourth path reflected in FIG. 7*a* is represented by the elution step wherein electrophoretic migration is not very influential or even non-existent as a component of each particle's net direction.

FIG. 7*a* shows such a ZE apparatus in which the samples are separated on the basis of their charge and to a lesser extent on the basis of their form and size. As indicated in FIG. 7*b*, the electrical conductivity profile 136 of the separation medium between the two electrodes included a high conductivity region 138 in the cathode space 28 and anode space 30, both of which are in the vicinity of the electrodes. These are shown in FIG. 7*b* as high conductivity regions 138, while the separation media is represented as a low conductivity region 140. The pH value is the same throughout the entire separation medium. The flat pH profile 134 is generated in the separation medium between the cathode and anode media buffers 170 and 172, respectively. While high pH regions 144 exist within the cathode and anode media buffers, a low pH region exists therebetween.

In a second mode of electrophoretic separation, separation is based on the different pI value of the particles to be separated, with this pI value being equivalent to the pH value of the surrounding, non-homogenous medium against which the particles appear neutral. FFE of particles on the basis of different isoelectric points allows analytes or particles with only minimal disparities in their pI values to be isolated. This is termed isoelectric focusing (IEF) carried out in free-flow electrophoresis (FFE). At the isoelectric point pI (i.e. at the point in the separation medium displaying the pH value at which the number of negative and positive charges is equal for a given particle, e.g. a protein molecule) the total charge or net surface charge of this particle is zero. The focusing effect inherent in the separation medium of an apparatus causes a particle which is diffused away from pI to automatically receive a (positive or negative) net surface charge and to be transported in the direction of pI again by the electrical field.

As a result of the charge transfer (i.e., electrical interaction) between analytes or particles with ionic molecules (preferably monovalent ions) of the separation medium, it is to be expected that there is a major change in the pI value and therefore a rapid and total separation of the complex consisting of the particle and the ionic molecule from the rest of the sample species. The cyclic isoelectric focusing technique is especially suitable for the preparative isolation of biopolymers in general as well as of bioparticles, the biological function or integrity of which is certain to be within the range of the selected span of pH gradients in the separation medium. By adding "osmotic expanders" it is possible to ensure that ideal osmotic pressure is maintained. For example, by adding uncharged substances (e.g. sucrose or mannitol, etc., as a non-ionic osmotic expander) and/or salts (e.g. NaCl as an ionic osmotic expander), optimal osmotic pressure (i.e. isomolal conditions) can be achieved for a given cell type (e.g., 250-310 mosmol for mammalian cells).

FIG. 8b shows an IEF electrophoresis apparatus 10 with a linear pH profile gradient 142. A separation medium flows in a laminar manner between both the electrodes as demonstrated within stage 2 and 3 of FIG. 2c. A sample with three groups of particles (90b, 104b, and 118b) to be separated is introduced into the separation medium via the sample inlet 38 and transported by the laminar flow of the separation medium. The three groups of particles are separated during stage 2 and 3 of the step in FIG. 2c, and are thereby allowed to focus and be collected in distinct fractions in the pH gradient resulting from the electrical field generated between the electrodes in the separation medium represented as stage 4 or FIG. 2d. Specifically, the paths of first particle 90b, second particle 104b, and third particle 118b are reflected in FIG. 8a. Each particle (90b, 104b, 118b) follows a special path or movement within stages 2 and 3 of electrophoretic migration. The particles have a pI that influences their movement within the separation space under conditions that enable electrophoretic migration within the IEF separation media. Third particle 118b has a pI slightly higher than the pI of the media near its original position, and therefore during the path of movement under IEF electrophoretic conditions, slightly deflects towards the cathode while the bulk fluid flow of the separation media influences net particle movement of third particle 118b with respect to the inlet and outlet ends of the chamber. Second particle 104b on the other hand has a pI much higher than the pI of the media near its original position, and therefore during the path of movement under IEF electrophoretic conditions, greatly deflects towards the cathode while the bulk fluid flow of the separation media influences net particle movement of second particle 104b with respect to the inlet and outlet ends of the chamber. First particle 90b on the other hand has a pI much lower than the pI of the media near its original position, and therefore during the path of movement under IEF electrophoretic conditions, greatly deflects towards the anode while the bulk fluid flow of the separation media influences net particle movement of first particle 90b with respect to the inlet and outlet ends of the chamber. It should be noted that FIG. 8a reflects an IEF separation wherein the particles never reached their pIs. If more cycles of forward and backward movement occurred, or if a longer period or duration of electrophoretic migration was allowed to take place, the particles would eventually reach their pIs and only experience movement forward and backward as would the bulk fluid flow of the sample and separation media. In all cases of the first, second, and third particles (90b, 104b, 118b) the fourth path reflected in FIG. 8a is represented by the elution step wherein electrophoretic migration is not very influential or even non-existent as a component of each particle's net direction.

FIG. 8b indicates the electrical conductivity profile 136 of the separation medium between the two electrodes with high electrical conductivity in the cathode space 28 and anode space 30 in the vicinity of the electrodes. These are shown in FIG. 8b as high conductivity regions 138, while the separation media is represented as a low conductivity region 140. The pH profile gradient 142 is generated in the separation medium between the cathode and anode media buffers 170 and 172, respectively.

Additionally, an apparatus 10 according to embodiments of the present invention can be carried out in the isotachophoresis mode (ITP). The ITP FFE separation technique is based upon the difference in the electrophoretic mobility value of the particles to be separated. In contrast to ZE FFE, separation is achieved in non-homogenous separation media and offers better dissolution due to the inherent "focusing effect". When single particles are diffused from a separated band of particles (e.g. proteins) during ITP these particles enter a medium with varying electrical field strength, resulting in the particles being accelerated or decelerated. The inherent focusing effect means that the slower or faster moving particles find their way into the dominant fraction again. While not shown schematically as above for zone and IEF electrophoresis techniques, the present invention shows tremendous value and results when used in an ITP mode of operation.

It will be appreciated by those skilled in the art that various combinations of these separation techniques (IEF and ZE FFE or IEF and ITP) are possible. For instance, it is possible to use different separation media at the same time within the electrophoresis chamber of the FFE apparatus, thereby employing different separation parameters simultaneously.

In other embodiments of the invention, it is contemplated that the cyclic interval mode can be carried out in multiple separation subspaces within separation space 34 between a single pair of electrodes. Low mobility boundaries (with high conductivity) between adjacent sub-spaces are defined by the adjacent flows of cathodic stabilization medium and anodic stabilization medium that are disposed between the subspaces. All media are typically introduced through their respective inlets via a pump such as a multi-channel peristaltic pump. For details of this method, it is referred to international application no. PCT/US06/016175, which is hereby incorporated by reference in its entirety.

Preferably, the separation medium is a matrix-free, aqueous medium. The choice of the buffer components depends on the application mode (ZE, IEF, or ITP) and the nature of the sample or the separation problem. Suitable buffer systems are generally known in the art, and are in some instances commercially available (e.g., from BD GmbH, Planegg, Germany). Preferred buffer systems for carrying out embodiments of the present invention are, for example, described in co-pending application US2004/101973, provisionally filed application U.S. Ser. No. 60/885,792, and U.S. Ser. No. 60/945,246, all of which are hereby incorporated by reference in their entirety. Particularly preferred for cyclic interval FFE as described herein are simple buffer systems comprising one buffer acid and one buffer base, especially if the separation is carried out in ZE or flat-gradient IEF mode.

In some embodiments of the invention, the anodic stabilization medium, which is typically aqueous, may for example comprise an acid selected from the group consisting of gluconic acid, glucuronic acid, acetylsalicylic acid, 2-(N-morpholino) ethanesulphonic acid (MES), and zwitterionic buffers (also called Goods buffers—see Good et al., Biochemistry 5, 467 (1966)). In some embodiments of the invention, the cathodic stabilization medium, which is typically aqueous, may comprise a base selected from the group consisting of N-methyl-D-glucosamine, tri-isopropanolamine and 2-[bis (2-hydroxyethyl) amino]-2-(hydroxymethyl)propane-1,3-diol (BISTRIS).

One possibility of improving electrophoretic separation is to maximize the period of time a sample is moving and interposed between an anode and cathode. To accomplish this, the average fluid velocity, duration, and distance of displacement for the bulk flow of media and sample can be adjusted to maximize the electrophoretic performance of the application. In some instances, for example, residence time might be of a major concern and therefore the number of cycles as well as the duration, distance, and linear particle speed for the bulk flow of separation media may be adjusted to optimize output and performance. In other applications, band broadening due to a laminar flow profile may be of interest to control. The flexibility of controlling the system parameters allows the user to maximize output and fractionation quality based on the type of application he or she is utilizing. The cyclic interval method according to the present invention provides the opportunity to perform any FFE-separation technique inside a single electrophoresis chamber 12. Moreover, the chamber may even be of shorter dimensions even at prolonged times of electrophoresis when compared to the chamber dimensions required by continuous free-flow electrophoresis machines.

As mentioned above, the present invention is particularly suitable for, but not limited to, the analysis and preparative separation of ions, peptides, biopolymers, bioparticles such as vesicles, cell membranes, cell organelles, viruses, etc., as well as synthetic polymers and generally any particles that may be influenced by an electrophoretic field.

It will be apparent to those of skill in the art that many modifications and variations of the embodiments described herein are possible without departing from the spirit and scope of the present invention as defined by the appended claims.

The invention claimed is:

1. A method for separating particles comprising:
disposing a separation medium and sample in an electrophoresis chamber having a top plate, a bottom plate and a plurality of electrodes parallel to one another with a separation space disposed therebetween, and a fluidic displacement system for conveying a separation medium between the electrodes;
applying a voltage between the electrodes effective to manipulate particles electrophoretically;
displacing at least a portion of the separation medium and sample towards a first direction parallel to the direction of the electrodes;
displacing at least a portion of the separation medium and sample in a second direction opposite the first direction, wherein the displacing steps occur in a single electrophoresis chamber.

2. The method of claim 1, further comprising the step of eluting the separation medium and sample from the electrophoresis chamber through one or more outlets.

3. The method of claim 2, wherein at least a portion of the separation medium and the sample is eluted from the separation space into individual collection cavities such as vessels or wells in microtiter plates.

4. The method of claim 2, wherein at least a portion of the separation medium and sample are eluted towards outlets by displacing the separation medium and sample in a direction consistent with the first or second direction.

5. The method of claim 2, wherein prior to eluting the separation medium and sample from the electrophoresis chamber, the method comprises removing the voltage between the electrodes effective to manipulate particles electrophoretically.

6. The method of claim 1, wherein applying a voltage between electrodes enables an electrophoretic separation mode chosen from the group consisting of isoelectric focusing, isotachophoresis, and zone electrophoresis.

7. The method of claim 1, wherein the top plate and bottom plate are stationary with respect to the electrodes and each other while applying the voltage.

8. The method of claim 1, wherein a cycle comprises:
displacing the separation medium and sample towards a first direction generally parallel to the direction of the electrodes, and
displacing the separation medium and sample in a second generation generally opposite the first direction; and
wherein the number of cycles is greater than one.

9. The method of claim 8, wherein a plurality of said cycles is selected so as to achieve sufficient separation of the sample.

10. The method of claim 1, further comprising the step of introducing and displacing a counterflow medium into the separation space.

11. An apparatus for separating particles comprising:
an electrophoresis chamber having a top plate, a bottom plate and a plurality of electrodes parallel to one another with a separation space disposed therebetween,
a fluidic displacement system configured to introduce a separation medium and to introduce a sample between the electrodes in a first direction parallel to the direction of the electrodes at a first flow rate; and
a second fluidic displacement system configured to cyclically displace the separation medium and sample between the first direction and a second direction opposite the first direction by introducing separation medium in the second direction at a second flow rate,
wherein the fluidic displacement system and second fluidic displacement system are configured such that a ratio of the first flow rate to the second flow rate is between about 1:10 to about 10:1.

12. The apparatus of claim 11, wherein the top plate and bottom plate are stationary with respect to the electrodes and each other.

13. The apparatus of claim 11, wherein the separation space between the top plate and bottom plate comprises a thickness of about 0.01 to about 1.5 mm.

14. The apparatus of claim 11, wherein the first fluidic displacement system comprises a multi-channel pump.

15. The apparatus of claim 11, wherein the fluidic displacement system for introducing a separation medium and introducing a sample between the electrodes is further used to remove the sample after separation from the separation space.

16. The apparatus of claim 11, wherein the second fluidic displacement system comprises a multi-channel pump.

17. The apparatus of claim 11, further comprising a controller configured to control the fluidic displacement systems.

18. The apparatus of claim 11, further comprising a controller configured to control the flow of current between the electrodes.

19. An apparatus for separating particles comprising:
an electrophoresis chamber defined by a top plate, a bottom plate and a plurality of electrodes parallel to one another with a separation space disposed therebetween,
a fluidic displacement system configured to introduce a separation medium and to introduce a sample between the electrodes in a first direction parallel to the direction of the electrodes at a first flow rate and configured to cyclically displace the separation medium and sample between the first direction and a second direction opposite the first direction by introducing separation medium in the second direction at a second flow rate,
wherein the fluidic displacement system is configured such that a ratio of the first flow rate to the second flow rate is between about 1:10 to about 10:1.

20. The apparatus of claim 19, wherein the top plate and bottom plate are stationary with respect to the electrodes and each other.

21. The apparatus of claim 19, wherein the fluidic displacement system comprises a multi-channel pump.

22. The apparatus of claim 19, further comprising electrode spaces configured to isolate the electrodes from the separation space.

23. The apparatus of claim 19, further comprising a fraction collector outlet configured to displace the separated fractions of the sample from the separation space into individual collection cavities such as vessels of well in microtiter plates.

24. A method for separating particles comprising:
disposing a separation medium and sample in an electrophoresis chamber having a top plate, a bottom plate, a first chamber end, a second chamber end, and a plurality of electrodes parallel to one another with a separation space disposed therebetween, the electrodes longitudinally extending toward each of the ends, and a fluidic displacement system for conveying a separation medium between the first and second chamber ends;
applying a voltage between the electrodes effective to manipulate particles electrophoretically;
displacing at least a portion of the separation medium and sample towards the first chamber end; and
displacing at least a portion of the separation medium and sample towards the second chamber end; and
subsequently displacing at least a portion of the separation medium and sample towards the first chamber end.

25. The apparatus of claim 11, wherein the electrophoresis chamber further comprises at least one sample inlet, a plurality of media inlets, and a plurality of counterflow inlets.

26. The apparatus of claim 19, wherein the electrophoresis chamber further comprises at least one sample inlet, a plurality of media inlets, and a plurality of counterflow inlets.

* * * * *